(12) United States Patent
Teraura et al.

(10) Patent No.: US 7,441,507 B2
(45) Date of Patent: Oct. 28, 2008

(54) MOVING DEVICE IN PIPE LINES

(75) Inventors: Makoto Teraura, Takarazuka (JP); Kazuhiro Suzuki, Takarazuka (JP)

(73) Assignee: Nippon Cable System Inc., Hyogo (JP)

( * ) Notice: Subject to any disclaimer, the term of this patent is extended or adjusted under 35 U.S.C. 154(b) by 415 days.

(21) Appl. No.: 11/167,089

(22) Filed: Jun. 28, 2005

(65) Prior Publication Data

US 2005/0284233 A1 Dec. 29, 2005

(30) Foreign Application Priority Data

Jun. 29, 2004 (JP) ............................. 2004-191302

(51) Int. Cl.
*B61B 13/10* (2006.01)
*B60L 13/04* (2006.01)

(52) U.S. Cl. .................................... 104/138.2; 104/282

(58) Field of Classification Search ............. 104/138.1, 104/138.2, 139, 281, 282, 284
See application file for complete search history.

(56) References Cited

U.S. PATENT DOCUMENTS

| | | | |
|---|---|---|---|
| 5,776,080 A | 7/1998 | Thome et al. | |
| 6,667,677 B2 * | 12/2003 | Yajima et al. | 335/220 |
| 6,689,119 B1 * | 2/2004 | Di Caprio et al. | 604/523 |

| | | |
|---|---|---|
| 2003/0214580 A1 | 11/2003 | Iddan |

FOREIGN PATENT DOCUMENTS

| | | |
|---|---|---|
| JP | 05-212093 A | 8/1993 |
| JP | 06-114037 A | 4/1994 |
| JP | 07-289504 A | 11/1995 |
| WO | WO 02/103721 A1 | 12/2002 |
| WO | WO 2004/047258 A2 | 6/2004 |

OTHER PUBLICATIONS

European search report dated Oct. 12, 2005.
European Search Report, Application No. 05105705.7—2305, dated Oct. 12, 2005.

\* cited by examiner

*Primary Examiner*—S. Joseph Morano
*Assistant Examiner*—Robert J McCarry, Jr.
(74) *Attorney, Agent, or Firm*—Cheng Law Group PLLC

(57) ABSTRACT

A moving device in pipe lines is provided, which allows easy switching of moving/stopping and remote control of the switching by only electric wires enabling easy operation in the inside of small diameter pipe lines.

The moving device 10 in pipe lines comprises a guide frame 11 in which a line of three or more coils 15, 16, 17 is interconnected flexibly in the direction of magnet flux, ring-shaped permanent magnets 19, 20, 21 provided around the periphery of the guide frame slidably in the direction of the shaft, and a control means such as computers etc. to control by a preset program selecting the direction of turning on of the coils.

22 Claims, 14 Drawing Sheets

Fig.6 a                    Fig.6 b
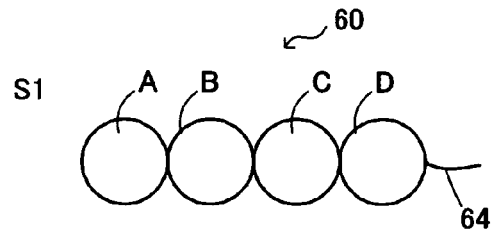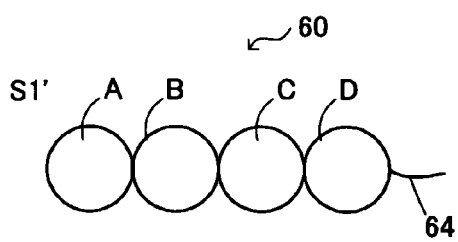
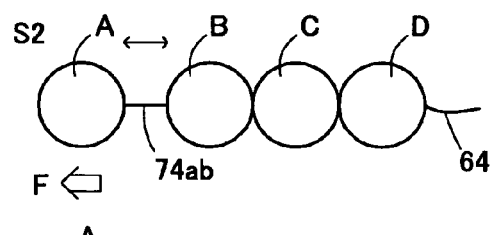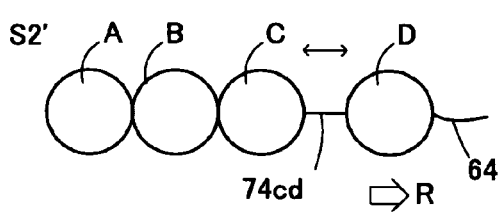
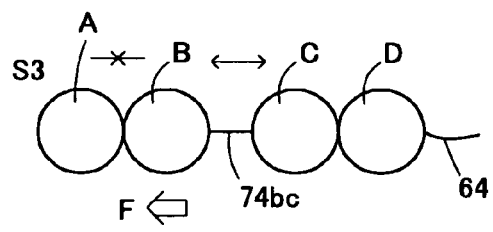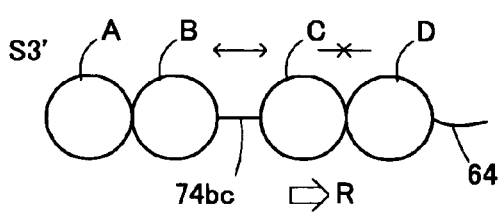
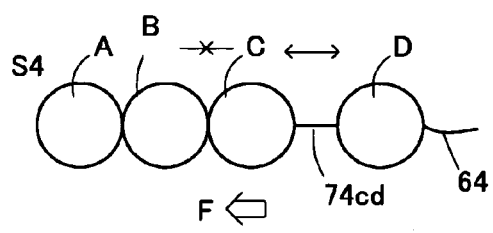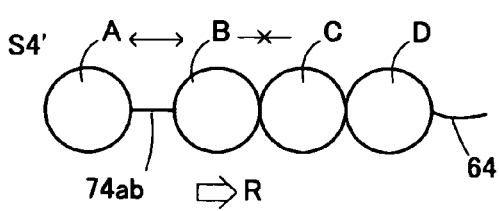
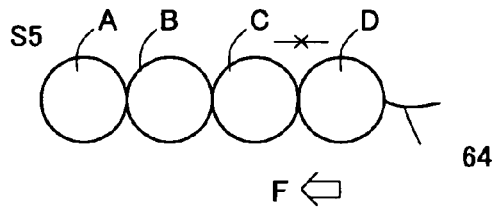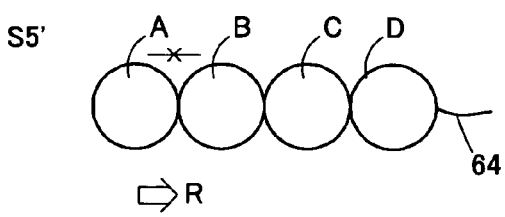

MOVING DEVICE IN PIPE LINES

FIELD OF THE INVENTION

This invention relates to a moving device in pipe lines, and more particularly to a moving device in pipe lines which moves/stops by being remote controlled or autonomously in body cavities or in pipe lines used for carrying various sensors to affected parts or to parts to be repaired, or for carrying and discharging medical agents such as curative medicines or mending agent for the part to be repaired.

BACKGROUND ARTS

Patent Document 1: Japanese Patent Laid Open No.1994-114037

Patent Document 2: Japanese Patent Laid Open No.1993-212093

Patent Document 3: Japanese Patent Laid Open No.1995-289504

In the Patent Document 1, a medical capsule which has plural capsules running along one guide wire inserted into a body cavity is disclosed. This is provided with a roller to tuck the guide wire in the capsule and a micro motor to drive the roller. The driven roller runs the capsule by the reactive force obtained from the guide wire. Further in the Patent Document 1, it is disclosed that plural pairs of electromagnets are provided on the each facing edge of the capsule in order to remote control the mutual angle between the capsules by magnetizing any of the electromagnet.

In the Patent Document 2, a medical capsule is disclosed, in which forward traveling legs and backward traveling legs, a bimorph transducer to vibrate the traveling legs, and covers to cover those traveling legs are provided. This capsule can move backward by covering the forward traveling legs with the cover to make the backward traveling legs only effective while the forward and the backward traveling legs are both activated. Similarly, it can move forward by covering the backward traveling legs with the cover.

In the Patent Document 3, a capsule endoscope unit is disclosed, in which balloons are provided front and rear and a self-advancing part connecting those balloons with retractable bellows.

The self-advancing part expands, for example, the front balloon to fix it to the inside wall of duodena etc., and deflate the rear balloon, and then retract the bellows to move the rear balloon forward.

Next, it expands the rear balloon to fix it to the inside wall, and deflate the front balloon, and then extend the front balloon to move the front balloon forward. By repeating this sequential process, it can move forward intermittently. Further, the self-advancing part can move backward by carrying out the sequential process in reverse.

DISCLOSURE OF INVENTION

In the capsule unit described in the Japanese Patent Document No.1, since the reaction force for the running is obtained from the guide wire, no force is applied to the inside wall of the body cavity. However, it is necessary to let through the guide wide previously requiring cumbersome insertion of the guide wire and the reinsertion of the guide wire in the cases of path changes. In the medical capsule described in the Japanese Patent Document No.1, the front traveling legs and the rear traveling legs are activated on a steady base, and the path change can be done by selecting any of the traveling legs to be covered. However, it is a cumbersome operation to block up the vibrating traveling legs with the covers, particularly it is a more cumbersome operation to change the position of the covers.

In the self-advancing part of the capsule endoscope unit described in the Japanese Patent Document No.3, the forward movement and the backward movement can be done by remote controlling the expansion/deflation of the balloons and the bellows. However, the balloons and the bellows take much time for injection/exhaust of air or liquid, and they require to secure pipe lines requiring a cumbersome operation. Further, any of them can not be manufactured in reduced size, therefore, no actual unit for small diameter tubular organs or pipe lines has not yet been put to practical use.

This invention is directed to provide a moving device in pipe lines that allows easy switching of moving/stopping, remote control of moving/stopping by only electrical wires, and further, easy operation in small diameter pipe lines.

The first aspect of a moving device in pipe lines of this invention (Claim 1) comprises an inside magnet line in which three or more magnet elements are interconnected in the direction of magnet flux, an outside magnet element line which is provided slidably on the outside of the magnet elements of the inside magnet line, a switching means which switches the magnet poles of the inside magnet elements and the corresponding pair of the outside magnet elements in-phase or reversed phase, a control means for controlling the each switching means by a preset program In such a moving device in pipe lines (Claim 2), the inside magnet elements are preferable to be interconnected flexibly each other. Further, the switching means comprises an electromagnet provided at least on one side of the corresponding pair of the magnet elements and a distributor for selecting the magnetic pole of the electromagnet (Claim 3).

The second configuration of a moving device in pipe lines of this invention (Claim 4) comprises a magnet line in which three or more electromagnet lines are interconnected, a guide member which guides the magnet lines slidably, and a distributor for controlling the electromagnet poles by a preset program.

In such second configuration of the moving device in pipe lines, the guide member is preferable to be a linear body let through the center of the magnets slidably and any of the electromagnets being fixed to the linear body (Claim 5), and the linear body is preferable to be flexible (Claim 6).

In the first configuration of a moving device in pipe lines of this invention, it is preferable that the control means comprises a controlling part which is located in the each switching means and a controller which gives instructions to move to the controlling part of the end magnet element pairs; the controlling part of the above pair of the magnet elements comprises a receiving part for receiving instructions to move, an operation part which performs an arithmetic operation of the magnets by the program in which the instructions to move obtained from the receiving part and the information of the object magnet pole of the magnet element are used as an argument, and a transmitting part which transmits the instructions to move to the next pair of the magnet elements after the switching part switches the magnet poles according to the operation part; the receiving part and the transmitting part transmits the instructions to move from the end pair of the magnet element to the front pair or from the front pair of the magnet element to the end pair in sequence (Claim 7).

In the second configuration of a moving device in pipe lines of this invention, it is preferable that the distributor is located in the each electromagnet and comprises the controlling part to control the poles of the electromagnet by a preset program and the controller which gives instructions to the controlling part of the end distributor; the controlling part of the electromagnet is provided with the receiver which receives the instructions to move, the operation part which performs an arithmetic operation of the magnets and controls the magnets by the program in which the instructions to move obtained from the receiving part and the information of the object magnet pole of the magnet element are used as an argument, and is provided with the transmitter which transmits the instructions to move to the controlling part of the electromagnet after the control of the pole by the operation parts; the receiving part and the transmitting part transmit the instructions to move from the end electromagnets to front electromagnets or from the front electromagnets to the end electromagnets (Claim 8).

The third configuration of a moving device in pipe lines of this invention (Claim 9) comprises three or more segments, an interconnecting means which interconnects these segments, a driving means which drives the interconnecting means so as to move these segments to the remaining segments relatively, and a control means to control the driving means, wherein the controlling means comprises a controlling parts provided in each segment and a controller which gives instructions to move to the end controlling part; the controlling part comprises a receiving part which receives instructions to move, an operation part which drives the driving means by computing the conditions of the object driving means using the information of the instructions to move obtained from the receiving part and the conditions of the object driving means as an argument, and a transmitting part which transmits the instructions to move to the controlling part of the other driving means after the control of the driving means by the operation part; the each receiving part and the transmitting part transmits the instructions to move from the end driving means to the front driving means or from the front driving means to the end driving means in sequence; the engaging force with the inside of pipe lines of the moved segments are smaller than that of the remaining segments.

Another aspect of a moving device in pipe lines of this invention (Claim 10) comprises three or more segments; an extendable interconnecting means for interconnecting these segments mately in a straight line retractably; and an extendable driving means for extending and retracting the extendable interconnecting means so as to move one or more segments selectively to the remaining segments relatively; wherein the engaging force with the inside of pipe lines of the moved segments is smaller than that of the remaining segments.

In such a moving device in pipe lines, it is preferable that each force for engaging with the inside of pipe lines of the segments are equal to azch other (Claim 11). And further, it is preferable that the extendable driving means is means for moving the each segment forward or backward selectively to the remaining segments (Claim 12). Additionally, it is preferable that the extendable driving means moves the segments from one edge to another edge in sequence (Claim 13).

And further, it is preferable that an arm for moving forward whose engaging force inside the pipe lines for moving forward is larger than that for moving backward is provided (Claim 14). Additionally, it is preferable that an arm for moving backward whose engaging force inside the pipe lines for moving backward is larger than that for moving forward is provided for at least one of the segments, and a direction selecting means for selectively moving the arms for moving forward and backward is provided (Claim 15).

The fourth aspect of the moving device in pipe lines of this invention (Claim 16) comprises an edge segment of the head side; an edge segment of the tale side; an extendable interconnecting means which interconnects these segments mately retractably and an extendable driving means which drives the extendable interconnecting means, the arm for forward moving is provided, the engaging force with the inside of pipe lines of which is larger than backward.

In such a moving device in pipe lines, it is preferable that the arm for moving backward is provided on each segment, the engaging force with the inside of pipe lines of which is larger than backward (Claim 17).

And further, it is preferable that an edge segment is swing-freely and retractably interconnected to the back of the tale side segment, an extendable driving means provided between the edge segment and the tale side segment (Claim 18). Additionally, it is preferable that an edge segment is swing-freely and retractably interconnected to the front of the head side segment, an extendable driving means provided between the edge segment and the head side segment (Claim 19).

And further, it is preferable that a moving device in pipe lines of this invention (Claim 20), a storage in which movement patterns of the segment and a controlling part which controls the movement of segments according to movement patterns of segments are provided.

The first aspect of a moving device in pipe lines of this invention (Claim 1) fundamentally obtains the driving force as a whole to move in reciprocate motion along the axis by switching alternatively between the attractive force and the repelling force of the magnet poles, wherein the poles of the magnet element of the inside magnet line and the outside magnet line are excited into inverse phase yielding an attractive force between the magnets and excited into in-phase yielding a repelling force between the magnets. For example, when it is excited into inverse phase wholly, the magnet elements attract each other to be lined up. Next, when it is excited into in-phase, since the outside magnet elements meet with resistance on the inside wall of the pipe lines, the inside magnet line all together moves to one side and attracts each other in a shifted position.

When the head inside magnet elements and the outside magnet elements are excited into reverse phase, the outside magnet elements intend to move so as to be lined up with the corresponding inside magnet line, and the other second plural magnet lines intend to stay in the former position. Resultantly, the head magnet element intends to move in between the two other outside magnet elements relatively, but since the resistance on the inside wall of the pipe line of the inside magnet elements is larger than that of the outside elements whose resistance is depending only on the head magnet element, the head outside magnet element only moves.

When the phase of the second outside magnet elements and the corresponding inside magnet elements only is switched to reverse phase, the second outside magnet elements only move as described above. Thus, the outside magnet elements are moved one by one in sequence, they move wholly in the direction of movement and return to the initial condition. Accordingly, by repeating the above cycles, the device can be moved wholly in peristaltic motion. The order to excite into reverse phase is not always necessary to be from the head but to be from the tale, or in random.

Further, it can be excited into in-phase at first from the head in sequence (or in random) and finally be excited into reverse phase wholly.

In the case that the inside magnet elements are interconnected flexibly each other (Claim 2), it is wholly flexible like beads and easy to move in bended or curved pipelines.

In the case that the switching means comprises an electromagnet provided at least on one side of the corresponding pair of the magnet elements and a distributor for selecting the magnetic pole of the electromagnet (Claim 3), switching one side of the magnet poles by the distributor can excite the magnet pole into reverse phase to the other magnet elements, thereby allowing easy remote control.

The inside magnet elements can be an electromagnet and the outside magnet element can be a permanent magnet, and inversely the outside magnet can be an electromagnet and the inside magnet can be a permanent magnet. Further, the inside magnet and the outside magnet can be both an electromagnet.

In the second aspect of the moving device in pipe lines of this invention (Claim 4), since the magnet lines arranged in lengthwise direction are electromagnets each other, by exciting the poles of the each electromagnet into in-phase or reverse phase, a drawing force or a removing force are applied. Therefore, as described above, it can be shifted one by one toward the direction of movement as a whole.

In the case that the guide member is a linear body let through the center of the magnets slidably and any of the electromagnets is fixed to the linear body (Claim 5), the line of the electromagnets can be interconnected into one body with simple composition, thereby a compact body being composed wholly.

When a flexible linear body is employed (Claim 6), each electromagnet is interconnected flexibly as beads allowing easy movement in bended or curved pipe lines.

In the first aspect of the moving device in pipe lines and in the case that the control means comprises a controlling part which is located in the each switching means and a controller which gives instructions to move to the controlling part of the end magnet element pairs; the controlling part of the above pair of the magnet elements comprises a receiving part for receiving instructions to move, an operation part which performs an arithmetic operation of the magnets by the program in which the instructions to move obtained from the receiving part and the information of the object magnet pole of the magnet element are used as an argument, and a transmitting part which transmits the instructions to move to the next pair of the magnet elements after the switching part switches the magnet poles according to the operation part; the receiving part and the transmitting part transmits the instructions to move from the end pair of the magnet element to the front pair or from the front pair of the magnet element to the end pair in sequence. (Claim 7), since the each switching means is controlled by the exclusive controlling part, the distance between the controlling part and the switching means or the controller can be reduced to prevent the occurrence of the time delay of communication. Further, since the computing is distributed to the each controlling part, the control cycle can be reduced compared with the case that all controlling parts are centrally controlled. Therefore, it can respond to instructions quickly allowing easy operation in small diameter pipe lines. Additionally, the programs can be standardized to reduce manufacturing cost and the maintenance is made more efficient. The standardization of the program allows easy check of the communication functions and other functions. In the case of troubles of each magnet element and extension/shortening of the length, disassembly or connection can be done easily.

In the second aspect of the moving device in pipe lines, wherein the distributor is located in each electromagnet and comprises the controlling part to control the poles of the electromagnet by a preset program and the controller which gives instructions to the controlling part of the end distributor; the controlling part of the electromagnet is provided with the receiver which receives the instructions to move, the operation part which performs an arithmetic operation of the magnets and controls the magnets by the program in which the instructions to move obtained from the receiving part and the information of the object magnet pole of the magnet element are used as an argument, and is provided with the transmitter which transmits the instructions to move to the controlling part of the electromagnet after the control of the pole by the operation parts; the receiving part and the transmitting part transmit the instructions to move from the end electromagnets to front electromagnets or from the front electromagnets to the end electromagnets (Claim 8), same as described above, the device responds quickly to the instructions, allowing easy operation in small diameter pipe lines.

In the third spect of the moving device in pipe line (Claim 9), since each connecting means is controlled by the exclusive controlling part, the distance between the controlling part and the connecting means or the controller can be reduced to prevent the occurrence of the time delay of communication. Further, since the computing is distributed to the each controlling part, the control cycle can be reduced compared with the case that all controlling parts are centrally controlled. Therefore, the device responds quickly to the instructions, allowing easy operation in small diameter pipe lines.

In another aspect of the moving device in pipe lines of this invention (Claim 10), the interval between the segments are extended/retracted by the extendable connecting means.

When the intervals of the some segment in the direction of movement are retracted and/or the intervals in the direction of backward movement are extended and the engaging force of the some segments with the inside of pipe lines is smaller than that of the remaining segments, the some segments can move in pipes in the direction of movement.

When each force of engaging with the inside of pipe lines of the segments are equal to each other (Claim 11), since the engaging force are equal, a moving device moves as the one did last time in the case of replacing the segment so as to maintenance or repair.

The moving device which can only move forward and cannot move backward can be usable in the application such as for passing through the pipe lines, but the moving device which can move forward/backward has more usability.

In the case that the extendable driving means for moving the each segment forward or backward selectively to the remaining segments (Claim 12), the device has such functions to move backward. The action of the backward movement is same as that of the forward movement. The combination of the forward and backward movement allows returning when the device moves too far, thereby the position adjustment is easy. Further, it can move in pipe lines which can not be passed through or, for example, stopped up in the front edge. Moreover, in the case that the pipe lines are provided with power, communication lines, or guide wires, they cannot be passed through in one direction, but the moving device which can move backward can intrude into the pipe lines and can return to the entrance, thereby such cables as above can be provided.

In the case that the extendable driving means moves the segments from one edge to another edge in sequence (Claim 13), at the beginning, the extendable driving means extends the front segment and the interconnected second segment, thereby the front segment only slips and moves in the direction of movement due to the difference of the engaging force. After that, it retracts the interval between the front segment and the second segment and extends the interval between the second segment and the interconnected third segment, thereby the second segment slips and moves toward the front segment as if being drawn. Further, by performing the same operation as the second segment to the third segment, the third segment is drawn toward the second segment. After performing such operation to the rear segment in sequence, the interval between the front segment and the second segment is extended again to move the front segment in the direction of movement. By performing such operation intermittently, the device can move in pipe lines.

And further, in the case that an arm for moving forward whose engaging force inside the pipe lines for moving forward is larger than that for moving backward is provided (Claim 14), engaging force inside the pipe lines of the head, body and tale segment can be supported and bigger engaging force inside the pipe linens can be obtained with fewer segments.

Additionally, in the case that an arm for moving backward whose engaging force inside the pipe lines for moving backward is larger than that for moving forward is provided for at least one of the segments, and a direction selecting means which selectively moves the arms for moving forward and backward is provided (Claim 15), the same way as engaging force inside the pipe lines of the head, body and tale segment can be supported and bigger engaging force inside the pipe linens can be obtained with fewer segments. Therefore a moving device can easily move.

In the fourth aspect of the moving device in pipe line (Claim 16), based on the engaging force difference, the arm moving forward itself by its nature slides in the forward direction and has resistance or friction by sliding. Therefore, engaging/releasing is not needed, and they move forward simply by retracting/extending the intervals between the segments of the head and the tale sides by the extendable connecting means. Namely, when the interval between the segments of the head side and the tale side is extended by extendable driving means, the arm of the tale side segment has resistance or friction by sliding with the inside wall of the pipe, and the arm of the head side segment slides for the inside wall of the pipe. Oppositely when the interval between the both segments is retracted, the arm of the head side segment has resistance or friction by sliding, and the arm of the side segment slides. In this way, with retracting/extending only, moving forward can be intermittently continued.

In the case that the arm for moving backward is provided on each segment, the engaging force with the inside of pipe lines of which is larger than backward (Claim 17), the moving device which can only move forward and cannot move backward can be usable in the application such as for passing through the pipe lines, but the moving device which can move forward/backward has more usability.

In the case that an edge segment is swing-freely and retractably interconnected to the back of the tale side segment, an extendable driving means provided between the edge segment and the tale side segment (Claim 18), when a moving device moves forward in curved pipe lines, stably moves forward by taking a distance of edge segment to tale side segment.

In a similar way, when an edge segment is swing-freely and retractably interconnected to the front of the head side segment, an extendable driving means provided between the edge segment and the head side segment (Claim 19), when a moving device moves backward in a curved pipe lines, stably moves backward by taking a distance of edge segment to head side segment.

In the case that a storage in which movement patterns of the segment and a controlling part which controls the movement of segments according to movement patterns of segments are provided (Claim 20), since a segment can be moved according to a engaging force inside pipe lines, the segment can be easily moved in various shaped pipe lines.

BRIEF DESCRIPTION OF DRAWINGS

FIG. 6a and FIG. 6b are pattern diagrams showing respectively the conditions of the forward movement and the backward movement of the third embodiment of the moving device of this invention;

FIG. 8a is a cross sectional side view of the medium segment of the third embodiment of the moving device, and the FIG. 8b is a partial perspective view of the FIG. 8a;

FIG. 10a is a longitudinal cross section of the arm segment of the moving device, and the FIG. 10b is an I-I line cross section of FIG. 10a;

BEST MODE FOR CARRYING OUT THE INVENTION

The embodiments of the present invention are described bellow with reference to the accompanying drawings.

Figure 1:
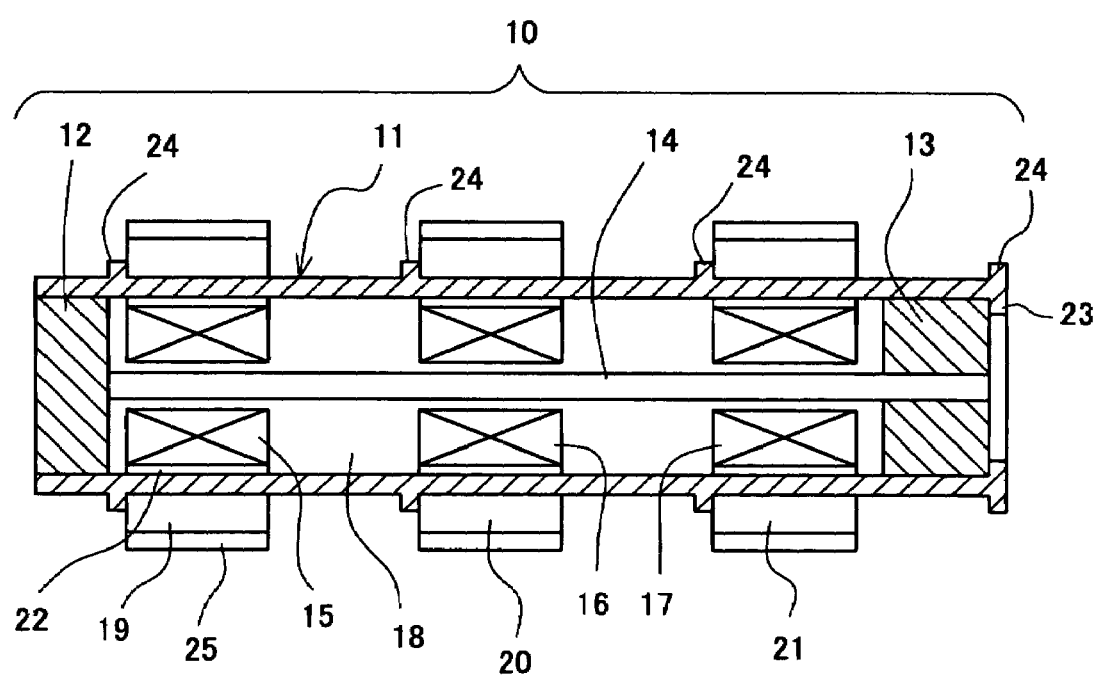
FIG. 1 is a cross section of the first embodiment of the moving device of this invention.

The moving device 10 shown in FIG. 1 comprises a tubular guide frame 11, a cap or a plug 12, 13 plugging the aperture of the both edge of the guide frame, a rod 14 with its both edge being supported by the plug 12,13 and located at the center of the guide frame 11. In the guide frame 11, surrounding or riding the rod 14, the ring-shaped first coil 15, the second coil 16, and the third coil 17 are fixed at a given interval. The part shown by Reference numeral 18 is vacant, but it can be filled. On the periphery of the guide frame 11, the ring-shaped first permanent magnet 19, the second permanent magnet 20, and the third permanent magnet 21 is provided slidably.

On the inside perimeter of the rear edge of the guide frame 11, an engaging projection 23 is provided, and on the periphery, an annular projection 24 to prevent the rear side plug 13 from dropping out is provided at an about equal interval. In this embodiment, the annular projection 24 is positioned so that when the permanent magnet 19, 20, 21 move forward and engage with the annular projection 24, they face the corresponding coil 15, 16, 17 respectively. When they move backward to engage with the annular projection 24, the vicinity of the front edge of the permanent magnet 19, 20, 21 correspond to the vicinity of the rear edge of the coils 15, 16, 17.

In this embodiment, the one annular projection 24 is used as the stopper both for the front permanent magnet and the rear permanent magnet, but two annular projections can be provided for the each permanent magnet stopper. In the case that the guide frame 11 is made flexible, the two annular projections can be separated and connected with a bellows. Then the rod 14 can be separated at the corresponding position and connected flexibly, or a flexible wire or a string can be used in place of the rod. The annular projection 24 can be omitted as described later.

The plug 13 is fixed to the inside of the guide frame 11 by adhesive bonding or screw cramp. Inside of the plug 13, batteries or control circuits can be located, or a container can be housed, in which medical agents etc. are charged and discharged in a given position. Some of the annular projections 24 are fixed by adhesive bonding after the permanent magnets 19, 20, 21 are mounted. The guide frame 11 is made of materials which pass through the magnetic line easily and is difficult to be magnetized i.e. nonmagnetic such as aluminum, stainless steel, synthetic resin, and rubbers.

The rod 14 acts as an armature to form a magnetic path of the coil 15, 16, and 17, and can be composed of the material such as mild steel wire, mild steel twisted wire, and pure iron etc. And also, flexible materials such as wires can be employed as described above. As the flexible materials, wire composed of twisted metal wires, twisted wire of synthetic fibers, string or tape composed of synthetic resin are used.

As the coils 15, 16, 17, a regular coil can be employed in which an insulated wire is winded around an annular core material to form an electromagnet. A groove 22 is provided around the each coil to pass through the lead wire of the coil. In this embodiment, three coils 15, 16, 17 are used, but four or more coils can be employed, in which case the same number of the permanent magnet 19, 20 21 are provided around the periphery of the guide frame 11.

The each permanent magnet 19, 20, 21 can be permanent magnet wholly, or they can be a piece of magnets adhered on the inner surface of the ring. The magnet pole is in the direction of the axis along which the magnetic flux flows. In the case of FIG. 1, the front side in the direction of movement is S pole, and rear side is N pole, but they can be magnetized in the inverse direction. Further, the magnet pole directions of the three electromagnets 19~21 are not necessary to be all together. The permanent magnets are preferable to be composed of the material having strong magnetism such as neodymium series, ferrite series, and Alnico series etc. In addition, in the embodiment of FIG. 1, on the periphery of the ring-shaped permanent magnet, a back yoke 25 is provided so as not to release the magnetic flux of the magnets.

There is no limit particularly in the size of the guide frame 11, and in the case that the device is let through the blood vessel, a degree of 0.2~2 mm in diameter, 5~20 mm in length is used. In the case that the device is let through the esophagus, a degree of 3~8 mm in diameter, 10~30 mm in length is used, and in the case that it is let through the small intestine, a degree of 5~10 mm in diameter, 20~40 mm in length is used respectively. In the case that it is let through a water pipe or an air duct, the size is suited for the each inner diameter. The coils 15, 16, 17 are connected to the each separate wire, and connected to the batteries located in the guide frame 11 through a switch to select the polarity. It can also be connected to an external distributor through a wire.

The method for turning on electricity and the action of the coils 15, 16, 17 of the moving device 10 is described next referencing FIG. 2. At the beginning, all of the coils 15, 16, 17 are turned on so as to be N pole in the front and to be S pole in the rear, thereby the polarity of the permanent magnets 19, 20, 21 corresponding to the coil 15, 16, 17 respectively become reverse phase, the corresponding permanent magnets 19, 20, 21 being attracted to the electromagnet of the coil each other (the first step S1).

Next, the direction of the turning on of all the coils is switched over so as to be S pole in the front and to be N pole in the rear, wherein the polarity of the permanent magnets and the coils is in-phase (the second step S2), thereby the permanent magnets and the coils repel each other and intend to be apart. However, as shown in FIG. 1, since the front edge of the each permanent magnet 19, 20, 21 is engaged with the annular projection 24, whole of the permanent magnets moves backward relatively to the guide frame 11. Then, because the periphery of the permanent magnets meets with resistance on the inside wall of the pipe lines, the coils 15~17 move forward all together resultantly receiving the reactive force. Therefore the N poles of the coil and the S poles of the permanent magnets attract each other at the forward shifted position to the permanent magnet.

After that, the pole of the front first coil 15 only is inverted to make the phase of the coil 15 reversed to that of the first permanent magnet 19 (the third step S3). Thereby, the front first permanent magnet 19 intends to move so as to be lined up with the first coil 15, and the other second permanent magnet 20 and the third permanent magnet 21 intend to stay in the former position. Thereby, the first permanent magnet 19 and the other permanent magnets 20 and 21 intend to be apart relatively. However, as for the resistance force with the inside wall of the pipe lines, added resistance force of the second permanent magnet 20 and the third permanent magnet 21 is larger than the resistance force only by the permanent magnet 19, thereby the front first permanent magnet 19 only move forward. In this occasion, the fact that the mass of the moving device 10 except for the first permanent magnet is much larger than that of the first permanent magnet 19 helps also the first permanent magnet only to move.

And then, when the pole of the second coil 16 is inverted (the forth step S4), same as above, only the second permanent magnet 20 corresponding the second coil 16 moves forward. Further, the pole of the third coil 17 is inverted to move the third permanent magnet 21 forward (the fifth step S5), thereby the condition returns to the first step S1. In order to control such turning on of the coils 15, 16, 17, it is preferable to accommodate a micro computer in the guide frame 11 or to set up a computer externally, and to control directly the direction of electric current flow of the power line of the each coil.

When the pair of the coil and the permanent magnet is more than four, the poles of the magnets are inverted in sequence as described above to move the corresponding permanent magnets forward. The more the pair of the coil and the magnets is, the larger is the difference between the resistance force on the inside wall of pipe lines of the one pair of the permanent magnet being set to move and that of the permanent magnet being set to stay, thereby the action described above becomes more secure. When the pair of the coil and the permanent magnet is more than six, they can be combined into three pairs to move all together. More specifically, the poles of the first coil, the forth coil, the seventh coil . . . are made into one set and their phase are inverted all together, the second coil, the fifth coil, the eighth coil . . . are made into one set, and the third coil, the sixth coil, the ninth coil are made into one set, and they are operated all together, thereby the one cycle time being shortened.

As above, the moving device 10 can be moved forward by repeating the one cycle from the first step S1 to the forth step in sequence along the arrowhead J1. In the shifting process from the second step S2 to the third process S3, and from the third step S3 to the forth step S4, to move forward the one permanent magnet only may cause to move it contrary to backward in an occasion that the one permanent magnet intended to moved has a particularly large frictional force due to the irregularity of pipe line walls, because it is based on the ground that the frictional force between the above permanent magnet and the pipe line wall is smaller than that of the sum of frictional force of the other permanent magnets. On the assumption of such occasion, it can also be composed so that the frictional force of the permanent magnet surface in the forward direction is smaller than that of the backward direction. For example, in the backward movement, an engaging projection which hooks the pipe line wall can be provided, or hairs projecting backward can be implanted for prevention measure of backward movement.

In the case that the moving device 10 is provided with power lines to transmit the power or control lines to control the pole of the coil line, these power lines or the control lines can be dragged in order to pull out or to move the advanced moving device 10 backward. The power lines and the control lines are extended from the rear edge of the moving device 10 (the right edge of FIG. 1). But in the case that the moving device is moved in a bended pipe line or in the case that a battery and a wireless communication are employed without use of the power lines and the control lines, the moving device 10 can be moved backward by itself by turning on the coils in the reverse procedure as described above. In other words, by operating from the fifth step S5 to the first step S1 shown in FIG. 2 along the arrow head J2, it can be moved backward in the reverse direction as described above.

Figure 2:
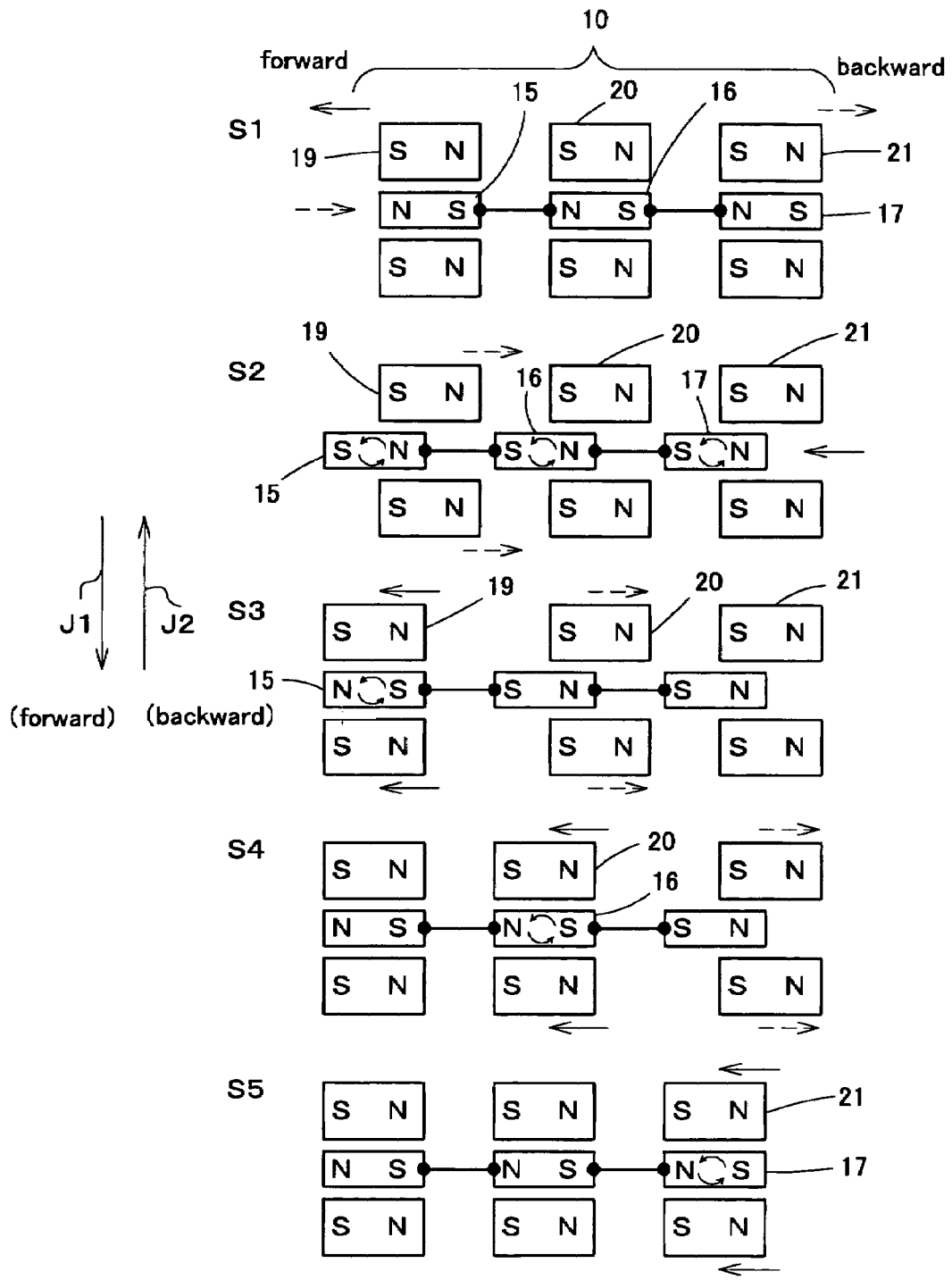
FIG. 2 is a process drawing showing the first embodiment of the operation procedure of the moving device of this invention.

More specifically, from the condition of the fifth step shown in FIG. 2, at the beginning, the pole of the third coil 17 is inverted to move the third permanent magnet 21 backward as shown by the dotted arrow head (the forth step S4, see the dotted arrow head), and then the pole of the second coil 16 is inverted to move the second permanent magnet 20 backward (the third step S3), next the pole of the first coil is inverted to move the first permanent magnet 19 backward (the second step S2), and finally whole poles of the coils are inverted all together to move the guide frame 11 (the first step S1), thereby it returns to the original condition i.e. the fifth step S5. Thus, the moving device in FIG. 1 moves forward when it is operated in the sequence along the arrowhead J1 shown in FIG. 2 and move backward when it is operated in the sequence along the arrowhead J2. Therefore, it is used exclusively for forward movement and is used also for forward and backward movement.

In such case that the device is used for backward movement as well as for forward movement, it is preferable not to be provided with the engaging projection or the implanted hair as the prevention measure for the backward movement as described above, or their actions are preferable to be composed as switchable between the forward movement and the backward movement.

In the embodiment shown in FIG. 1 and FIG. 2, the leftward movement in the figure is described as the forward movement and the rightward movement is described as the backward movement, but it can be described inversely that the rightward is as the forward movement and the leftward is as the backward movement. In this case, the power lines and the control lines are extended from the left of FIG. 1.

Figure 3:
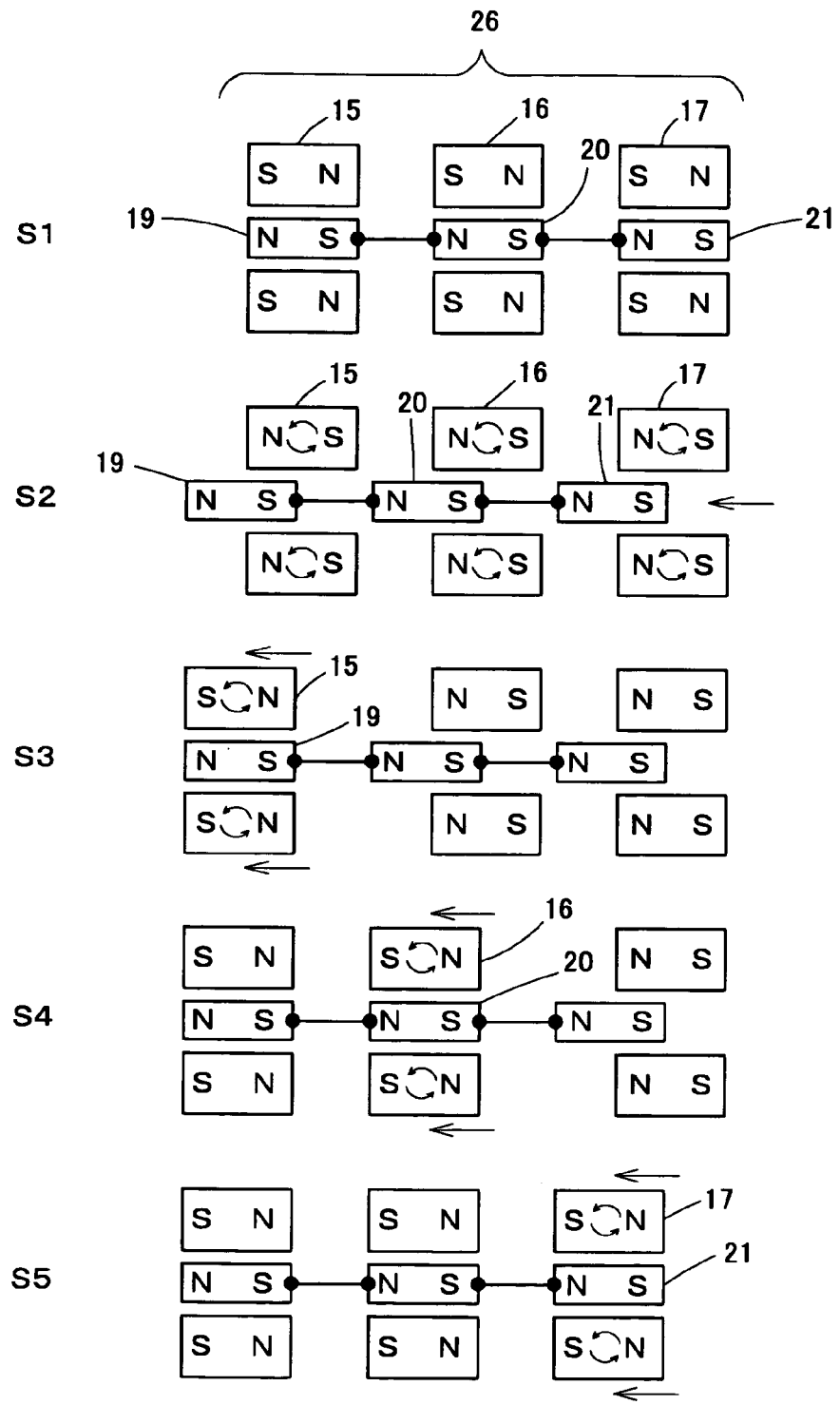
FIG. 3 is a process drawing showing other embodiment of the operation procedure of the moving device of this invention.

In the above embodiment, the coils are located at the center side and the permanent magnets are located at the outside, but such as the moving device 26 in FIG. 3, the permanent magnets 19, 20, 21 can be located at the center side and the coils 15, 16, 17 can be located at the outside. FIG. 3 shows the switching procedure of the pole of the coil and the process of movement. In the moving device shown in FIG. 3, the description is omitted because the process is substantially same as FIG. 2 excepting that the inside and the outside are reversed.

In the moving device 10 in FIG. 1, the annular projection 24 is provided around the periphery of the guide frame 11 to restrain the inverse direction movement of the permanent magnet. This is to prevent the coils 15~17 moving backward by the repelling force in the shift from the first step S1 to the second step S2 in FIG. 2 as described above. Accordingly, for example, the provision of auxiliary means to determine the initial direction of the permanent magnets 19, 20, 21 such as auxiliary coils in the vicinity of the each coil 15, 16, 17 allows omitting the projection 24.

Figure 4:
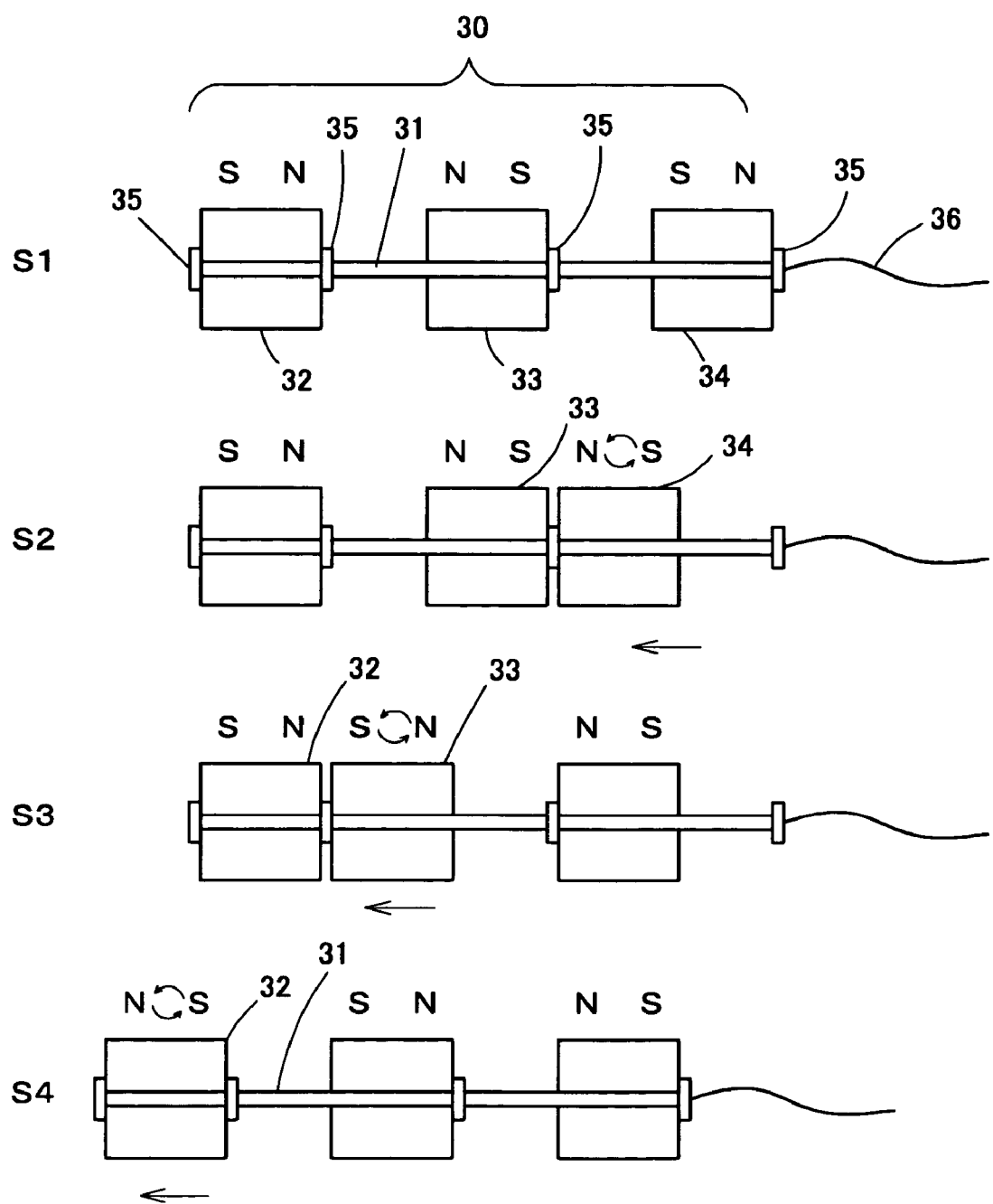
FIG. 4 is a process drawing showing the second embodiment of the operation procedure of the moving device of this invention.

In the above embodiment, the device is moved forward by utilizing the attracting and repelling action of the each inside and out side magnet elements to move back and forth relatively, but as shown in FIG. 4, the axial attracting force and repelling force of the magnet elements can be utilized. The moving device 30 in FIG. 4 comprises a guide shaft 31 and electromagnets 32, 33, and 34 slidably provided on the perimeter of the guide in the direction of the shaft. The guide shaft 31 is provided with a stopper 35 to restrain the moving range of the electromagnets 32~34. The first electromagnet 32 is interconnected to the guide shaft 31 to move all together. As the guide shaft 31, a flexible wire is used, but it can be a rigid rod or pipe. The reference numeral 36 in FIG. 4 is a power line to turn on the electromagnets 32, 33, and 34.

In this moving device 30, the direction of the poles is set alternatively so as to make the neighboring electromagnets to repel each other. More specifically in this embodiment, at the first step S1, the first electromagnet 32 is made to be S pole in the front edge and N pole in the rear edge, the second electromagnet 33 is made to be N pole in the front edge and S pole in the rear edge, and the third electromagnet 34 is made to be S pole in the front edge and N pole in the rear edge.

From this condition, the pole of the third electromagnet 34 is inverted to be N pole in the front edge and S pole in the rear edge (the second step S2), thereby the rear edge S pole of the second electromagnet 33 and the front edge N pole of the third electromagnet 34 attract each other to move the third electromagnet 34 forward same as that shown in FIG. 2.

And then, the pole of the second electromagnet 33 is inverted to be S pole in the front edge and N pole in the rear edge (the third step S3), thereby the rear edge N pole of the first electromagnet 32 and the front edge S pole of the second electromagnet 33 attract each other, and at the same time, the rear edge N pole of the second electromagnet 33 and the front edge N pole of the third electromagnet repel each other to move the second electromagnet 33 forward.

Next, the pole of the first electromagnet 32 is inverted to be N pole in the front edge and S pole in the rear edge (the forth step S4), thereby the rear edge S pole of the first electromagnet 32 and the front edge S pole of the second electromagnet 33 repel each other to move the first electromagnet 32 forward together with the guide shaft 31.

This condition is the same as that of the first step S1 excepting that the direction of the pole is reversed. Further, from this condition, by switching the direction of the pole of the third electromagnet 34, the second electromagnet 33, and the first electromagnet 32 in sequence which are about similar to the first step S1, the second step S2 and the third step S3, the condition returns to the original condition same as the first step S1.

In the case that the moving device 30 is moved backward, the direction of the poles of the electromagnets 32, 33, 34 are switched from the force step S4 to the first step S1 in the reverse sequence as described above. But it can be made to be a moving device exclusively for forward movement. In this case, on the periphery of the electromagnet, the preventive measure for the backward movement such as the projection or the implanted hair described above is preferable to be provided.

In addition, in the moving device 30 shown in FIG. 4, the guide shaft 31 is fixed to the first electromagnet 32 and the other electromagnets are left free to move along the shaft, but the guide shaft 31 can be fixed to the second electromagnet 33 or third electromagnet 34 and other electromagnets can be left free. In order to invert the pole of the electromagnets, the direction of the turning on of the electromagnet coil is inverted similarly with the moving device 10 in FIG. 1.

In the embodiment described above, as a means to change the direction of the pole of the magnet elements by a remote control, the electromagnets and the distributors to change the direction of current flows are employed. But by accommodating the distributor in the guide frame, an external switching of the signal can be limited only to switch between forward movement/off (or forward movement/off/backward movement). Further, such composition can be employed also that in place of the electromagnets, permanent magnets are accommodated rotatably in the case, and the rotation angle of the permanent magnets is remote controlled.

Figure 5:
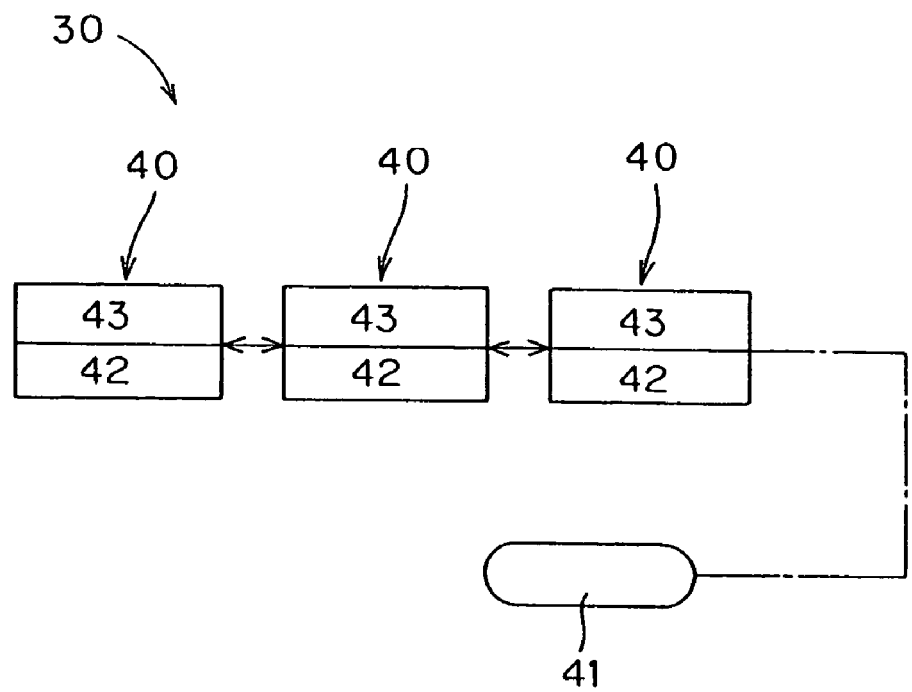
FIG. 5a is a rough flow chart showing the control of the second moving device.
FIG. 5b is a rough drawing of the control means.
Figure 5:
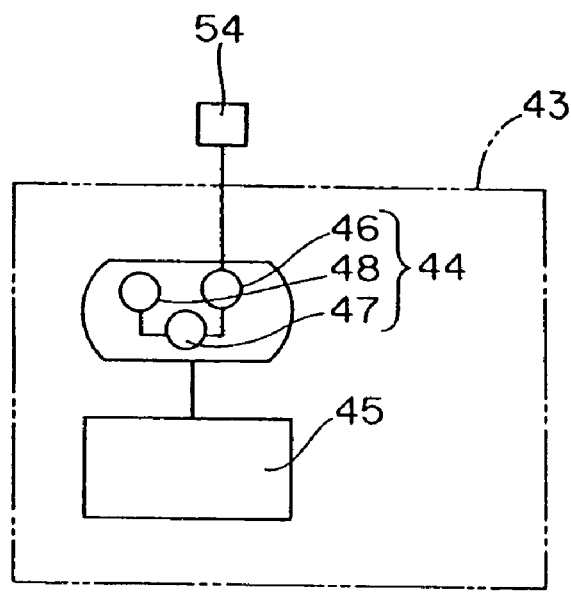

The rough control block diagram of the moving device in the second embodiment in FIG. 5a is shown. In FIG. 5a, the plural electromagnets (moving part 40) in the moving device 30 which move forward and backward in the pipe lines and the controller 41 which outputs the instructions to move to the moving part 40 are shown in a simplified figure. The above three moving part 40 are almost the same, but they are so designated that the one connected to the controller 41 is the end moving part 40, the one placed at the front edge is the front edge moving part 40, and the remaining one placed between the front edge and the end edge is the medium moving part 40. The moving device 30 comprises three moving part 40, but it can be extended by increasing the medium moving part 40.

The each moving part 40 is provided with a mechanical part 42 driving the each moving part 40 and a driver 43 controlling the mechanical part 42. The above mechanical part 42 corresponds to the coil provided in the each electromagnet of the moving device 30. And in the case of the moving device 10 or 20, the above mechanical part 42 corresponds to one pair of the inside and the outside coil and the magnets.

As shown in FIG. 5b, the driver 43 comprises a switching means 44 for inverting current direction to invert the pole of the above described electromagnet and a controlling part 45 to control the switching means 44 by a preset program (see FIG. 5b.)

The controller 41 is connected to the end edge moving part 40 and gives instructions to move only to the moving part 40. As the instructions used by the controller 41 can be such that instructs forward movement/stop only, that instructs backward movement/stop only, and that instructs forward movement/backward movement/stop. In addition to the instruction to stop of the moving device, an instruction to be standby for suspending the moving device can be used.

The above controlling part 45 comprises a receiving part 46 which receives a pole information of the self electromagnet that is the object of the control and also receives instructions to move from controlling part 45 of the neighboring other moving part 40, a computing part 47 which computes the pole by the above program from the pole information obtained from the receiving part 46 and instructions to move, and a transmitting part 48 which transmits the instruction to move to the controlling part 45 of the moving part 40 after the switching means 44 switches the pole according to the computing part 47.

Next, the conditions of the movement of the moving device 30 are described. The moving part 40 is, as shown in FIG. 4, is in either of the condition that it is in the backward movement contacting the rear stopper 35 or that it is in the forward movement contacting the front stopper 35. The condition is detected by a photo sensor, a limit switch or HALL IC provided in the moving part 40 or by a position sensor 54 (see FIG. 5a) described later, and the position information is transmitted to the receiver 46 of the driver 43.

At the beginning, the instruction to move forward or to move backward to the moving device 30 is transmitted by the controller 41 to the receiving part 46 of the end edge moving part 40. The receiving part 46a transmits the instruction to move forward or to move backward to the computing part 47. The computing part 47 computes the self movement using the position information from the position sensor 54 and the instruction to move forward or to move backward.

For example, in the case that the condition of the backward movement is detected by the position sensor 54 and the instruction to move forward is output by the controller 41, the switching means activates the mechanical part 42 to move forward. At the same time, in the case that the forward movement is detected by the position sensor 54 and the instruction to move forward is output by the controller 41, the mechanical part 42 is not activated. In the case that the mechanical part 42 is activated in the condition of forward movement, after the completion of the forward movement is detected by the position sensor 54, the transmitting part 48 transmits the instruction to move forward to the adjacent front medium moving part 40. On the other hand, in the case that the end edge mechanical part 42 is not activated, the transmitting part 48 directly transmits the instruction to move forward to the adjacent front medium moving part 40. Such operation patterns of the each moving part 40 are controlled by a control table (program) created from the instruction of the controller 41 to move forward or backward and the position information by the position sensor 54.

The above medium moving part 40 starts its motion making it a trigger to receive the instruction to move forward or backward from the end edge moving part 40. Since the process that the medium moving part 40 receives the instruction to move forward or backward from the end edge moving part 40 and transmits the instruction to the front edge moving part 40 is same as that of the end edge moving part 40, the description is omitted.

Same as the medium moving part 40, the front edge moving part 40b starts its motion making it a trigger to receive the instruction to move forward or backward from the medium moving part 40. The front edge moving part 40 transmits the instruction to move forward or backward to the medium moving part 40, and this time the signal is transmitted from the front edge to the end edge.

Further, the each moving part 40 exchange the each electromagnet information between the other moving parts 40 at a given interval.

Using the obtained magnet information and the computing table created from the self magnet information, it is possible to make the each moving part to search the next motion. In this case, the each moving part 40 transmits the self magnet information together with the self address to the other moving part 40. The each moving part 40 uses the instruction to move forward/backward as a trigger, but the pole information from the adjacent front or rear moving part 40 or the detected signal from the position sensor 54 can be also used as the trigger for starting to move.

In the case to halt the moving device 30, the controller 41 transmits a stop signal to the end edge moving part 40 and the stop signal is sequentially transmitted to the front edge moving part 40. Further, in the case that the power of the each moving part 40 is supplied from the controller 41, the moving device 30 can be halted by cutting the power supply from the controller 41 to the moving parts 40. In addition, the holding of the magnetized condition of the each electromagnet prevents the moving device from unintended operation when the power is turned on again.

Further, in the moving device 10, 26 (see FIG. 2 and FIG. 3), the same control method as described above can be applied. In this case, a process to change the whole poles (see S2 in FIG. 2 and FIG. 3) is required when the forward or backward movement is started. In the process S2, the instruction to move forward or backward is transmitted to all moving parts 40 from the controller 41. And then, the position sensor 54 detects whether the outside electromagnets and the inside electromagnets are separating or approaching. When the electromagnets are separating, the poles of the magnets are inverted to approach each other. At the same time, when they are approaching, it can be left to do nothing. These initial actions can be defined in the control table of the initial action separately in the controlling part 45.

Since the each moving part 40 of the moving device 30 is controlled by the exclusive driver 43, the distance between the driver 43 and the mechanical part 43 or the controller 41 can be shortened to make the problems of the communication time delay difficult to occur. Further, the distribution of the computing to the each driver 43 enables to shorten the control cycle compared with the case that the all drivers 43 are centrally controlled, thereby the response to the instructions becomes quick allowing easy operation in a small diameter pipe.

As the mechanical part 42, those operated by the variation of the poles are described above. Subsequently, the device which is operated by extending or retracting the mutual spacing in between the moving part 40 using an extendable part is described. Thereinafter, the third embodiment of the moving device employing such extendable part is described.

The moving device 60 shown in FIG. 6a is composed of four segments (the moving part 40) that are a segment A, a segment B, a segment C, and a segment D starting from the left. These segments are interconnected linearly and slidably by an extendable part 74 (extendable connecting means). The above extendable part 74 corresponds to the mechanical part 42 in FIG. 5a. In this figure, the mutual contacting part of the segments shows the retracted condition of the extendable part 74, and the extended condition is shown by the crossbar. To the rear segment D is connected an electric wire 64 to supply power for extending the extendable part 74 or a communication line to transmit instructions to segments for forward/backward movement. In this embodiment, the engaging force of these four segments with the inside of pipe lines are almost the same each other. Further, the each extendable part 74 is controlled by the driver 43 provided in the segment connected to the back of the extendable part 74, and its condition of the extension/retraction is detected by the position sensor 54 provided in the each segment (see FIG. 5b). The extendable part corresponds to the mechanical part 42 in FIG. 5a.

The material of the segments is properly determined depending on the material of the inside of the pipe lines. Particularly in the case that the pipe lines are those within the human or animal body etc, the segment material is preferable to be stainless steal or Titanium, and especially preferable to be Titanium. As the extendable part 74 which extends/retracts the interval in between the each segment, motors can be used and it can also be the above describe magnets, voice coil motors, hydraulic pressure or oil pressure cylinders which operate similarly.

The motion of thus composed moving device 60 is described using FIG. 6a. At the beginning, from the starting condition. (S1) in which the all extendable parts 74 are retracted, there is a process (S2) in which the extendable part 74ab located between the front segment A and the interconnected segment B is extended to widen the interval between the segment A and B. In this embodiment, since the engaging forces of the each segment in pipe lines are almost the same, the engaging force of the segments is determined by the number of the segments. Resultantly, in this process S2, the engaging force of the segment A with the inside of pipe lines is smaller than those of the remaining three segments, the segment A moves toward the arrowhead F in the figure.

And then, there is a process (S3) in which the extendable part 74ab between the segment A and the segment B retracts and the extendable part 74bc located the segment B and the segment C is extended. In this process (S3), regarding the segment B the interval in between the segment A is shortened and the interval in between the segment C is widen. Resultantly, by the difference of the engaging force with the inside of pipe lines, it is drawn toward the segment A side. Via the process S4 same as the case of the segment A, the segment C moves toward the arrowhead F of the inside of pipe lines (Process S4). Finally, the extendable part 74bc located between the segment D and the segment C is retracted to move the segment D toward the arrowhead F and drawn toward the segment C (S5). After completion of the process to S5, by repeating the process going back to the S1, the moving device 60 moves toward the arrowhead F in pipe lines.

Figure 7:
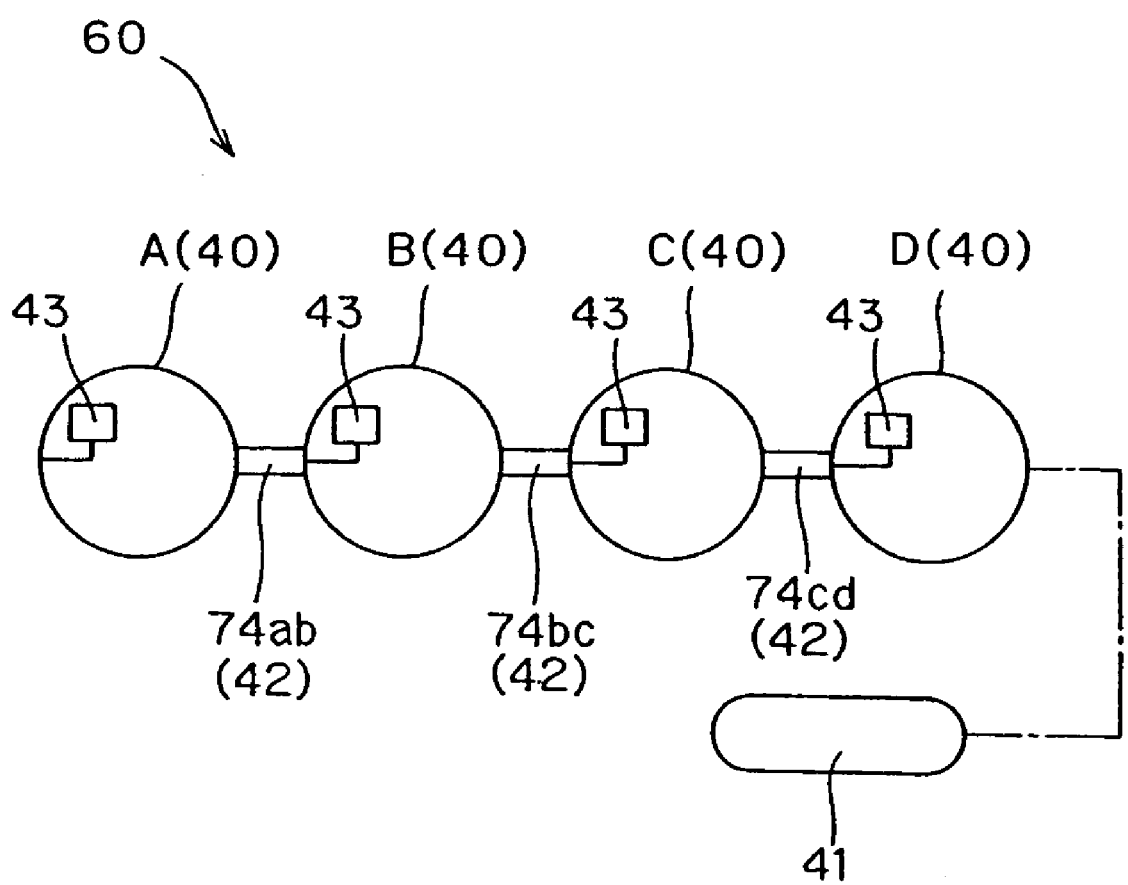
FIG. 7 is a rough block diagram of the control of the third embodiment of the moving device.

FIG. 7 shows the control block diagram of the moving device 60. The moving device 60 shown in the block diagram comprises plural moving part 40 (segment) same as those of the moving device 30. And the moving device 60 comprises the front edge segment A (the front moving part 40), the end edge segment D (the end edge segment 40), and the segment B and C between the front edge segment and the end edge segment (the medium segment 40, 40).

The segment B, C and D are provided with the driver 43 which is the same as that of the moving device 30 (see FIG. 5b), therefore the description is omitted assigning the same numeral for the same part.

The extendable part 74ab, 74bc, and 74cd are extended from the segment B, the segment C and D respectively, and are controlled by the drivers 43 provided in the each segment. The extendable part 74 corresponds to the mechanical part 42 in FIG. 5a and is operated by the switching means 44 located at the driver 43.

Back to FIG. 7, since in the backward of the segment D no segment is located, the segment D can push the segment C by the extendable part 74cd of the segment D to "extend" but is never pushed from the backward. Therefore, in order to move forward by itself, the extending part 74cd of the segment D must be "retracted". On the other hand, the front segment A can move by "extending" or "retracting" of the extendable part 74ab of the backward segment B. For that reason, the driver 43a and the mechanical part 42a are not mounted on the front segment A of the moving device 60.

In contrast, the medium segment C must "retract" the self extendable part 74*bc* at the same time when the extendable part 74*cd* of the backward segment D "extends" and pushes. Therefore, it is necessary for the extendable part 74*cd* of the segment D and the extendable part 74*bc* of the segment C to cooperate each other. It is also true between the extendable part 74*bc* of the segment C and the extendable part 74*ab* of the segment B.

For the above cooperated action, the driver 43 of the each segment of the moving device 60 transmit the information of the condition (being extended or being retracted) of the self extendable part 74 obtained from the position sensor 54 to the adjacent other drivers 43, and receives the information of the condition being extended/retracted of the extendable part 74 of the other drivers 43.

The control flow of the moving device 60 composed as above is described using FIG. 7 and FIG. 5*a*. From the controller 41 to the receiving part 46 of the end edge segment D (see FIG. 5*b*), the instruction to move forward/backward is transmitted. From the position sensor 54 of the segment D, the condition of the extendable part 74*cd* of the segment D being extended/retracted is transmitted. Further, from the forward segment C, the condition of the extendable part 74*bc* of the segment C being extended/retracted is transmitted. And the transmitted information is sent to the computing part 47 of the segment D. This information is computed using the control table (program) showing the condition of the corresponding extendable part 74*cd* of the segment D being extended/retracted. The results of the computing are, for example, "to extend the extendable part 74*cd*" of the segment D, "to retract the extendable part 74*cd*," or "nothing to be done" etc.

In the case that the result of the computing is "nothing to be done", the segment D transmits the information of the condition of the extendable part 74*cd* being extended/retracted and the instruction to move forward/backward to the forward segment C from the transmitting part 48 of the segment D (see FIG. 5*b*). The instruction to move forward/backward from the controller 41 can be transmitted from the end edge segment D in sequence to all the segments in the initial stage action of the controller 41.

In the case that the result of the computing is "to extend the extendable part 74*cd*" of the segment D, since it must cooperate with the forward segment C, the instruction "to extend the extendable part 74*cd*" is transmitted to the segment C from the transmitting part 48 of the segment D. When the segment C receives the information "to extend the extendable part 74*cd*", it "retracts" the extendable part 74*bc* of the segment C to cooperate with the segment D. When the segment D detects the completion of the action of the extendable part 74*cd* by the position sensor 54*a*, it transmits the information that the extendable part 74*cd* of the segment D is " being extended" and the instruction to move forward/backward from the controller 41 to the receiving section 46 of the segment C from the transmitting part 48.

The receiving part 46 of the segment C acts almost similarly as the above segment D. In other wards, the segment C receives the information of the condition of the extendable part 74*bc* of the segment C being extended/retracted, the condition of the extendable part 74*ab*, 74*cd* of the adjacent segment B, D being extended/retracted, and the instruction to move forward/backward transmitted from the segment D. Then the information is sent to the computing part 47 of the segment C and is computed using the control table for the segment C. In this case also, in order to "extend" the self extendable part 74*bc*, it is necessary to cooperate with the forward segment B. On the other hand, in the case of "nothing to be done", the extendable part 74*bc* is left actionless, and the condition of the extendable part 74*bc* being extended/retracted and the instruction to move forward/backward are transmitted to the segment B.

Thus, it acts in sequence to the segment B, next, it acts from the front edge segment toward the end edge segment C similarly to the forward movement. In order to stop the action, it is enough to cut the supply power to the segments. Moreover, when the power is turned on, it is preferable to hold the condition of the extendable parts 74 to be in the former condition of being extended/retracted.

In addition, each segment exchanges each other the information being extended/retracted between the mutual adjacent segments, but each segment can also get the information being extended/retracted of the other segment except for one self. In this case, address etc. for each segment is attached, and together with the address, the information bring extended/retracted etc. are transmitted. The driver 43 of the each segment obtains the extending/retracting action of the extendable part 74 from the information. In this case, it is preferable to synchronize the each segment by a synchronization signal of a given interval so as to make the adjacent segment 74 cooperate to act.

When this moving device 60 is moved backward, as shown in FIG. 6*b*, it is operated by the reverse procedure as shown above from S1', S2', S3', S4', S5' in sequence from the rear edge segment D to the segment A in the direction of the arrowhead R. After the S5' action ended, the process begins from S1 again, thus the process is repeated to move the moving device 60 in the direction of the arrowhead R in pipelines. In the case of the backward movement, the each segment action is controlled by the control table same as above.

In this embodiment, the device is composed of the four driving segments, but as for the number of the segments, for example, five or ten of the segments can be connected in series to move as described above. In this case, by varying the number of segments to be moved in each process enabling the variation of the engaging force with the inside of pipe lines, it can respond to the variation of the engaging force with the inside of pipe lines. Further, in one moving device, plural segments can be moved in one process, and plural moving points can be provided in one process. Moreover, engaging arms etc. to increase the engaging force with the inside of pipe lines can be provided in the each segment. In this case, the increased engaging force of the segments enables to decrease the number and the weight of the segments providing smaller and convenient devices. Further, the number of the signal lines can be decreased, since each neighbor segments are interconnected with the signal lines. And in the case of failures, the failed parts can be controlled by the driver of other segments, the failed parts only can be easily replaced.

In the case that the movement of the segments is more complicated, the provision of such a controlling device enables to cope with more various inside of pipes that has a storage in which movement patterns of the several kind of segments are stored and execute the above pattern responding to the conditions in the pipe lines and to the speed of the movement. Such composition allows the controlling part to control the moving device securely by storing the engaging force of the each segment in the above storage media for the case that the engaging forces of the each segment with inside of pipe lines are not about equal as described above. In this storage, the history of the previous motion can be stored and be played back.

Figure 8:
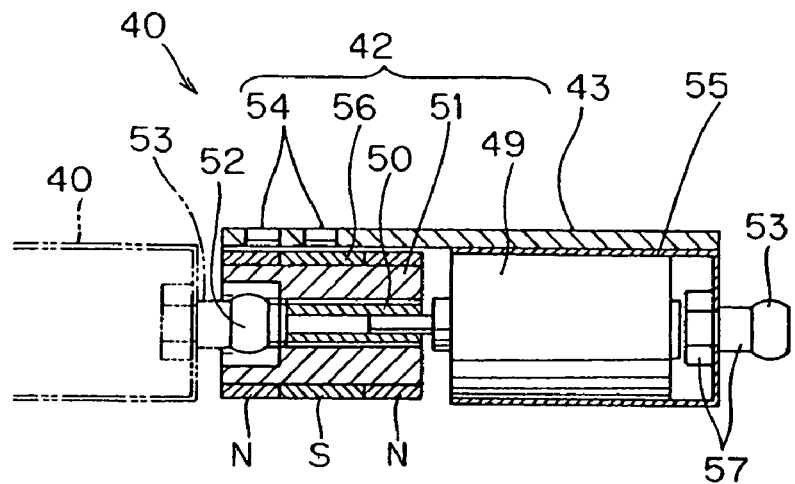
Figure 8:
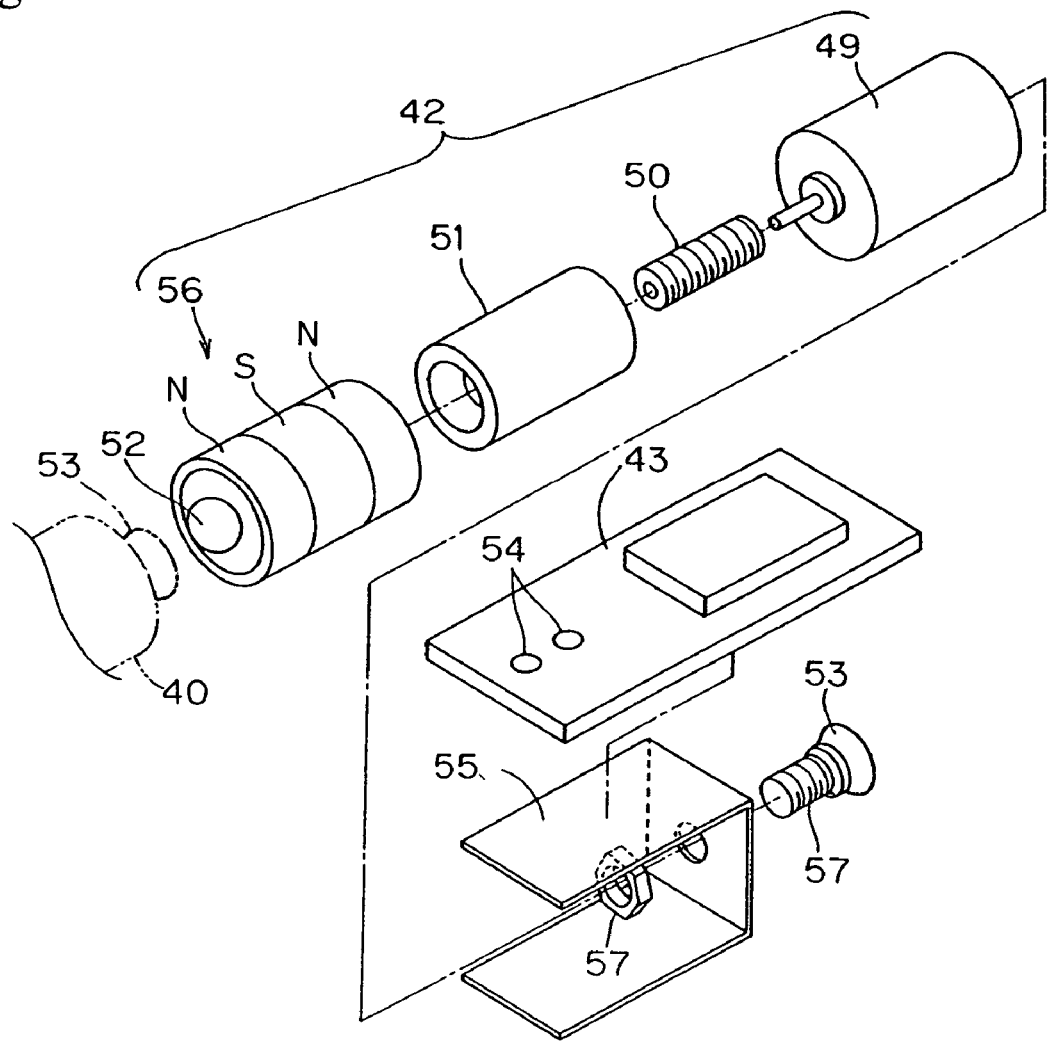

The embodiment of the moving device 60 is shown in FIG. 8*a* and FIG. 8*b*. FIG. 8*a* and FIG. 8*b* show the medium segment C or D. Since the segment D has many common parts with other segments, this segment is described here and the descriptions of the other segments are omitted. The above segment D comprises the mechanical part 42, the driver 43 which drives the mechanical part 43. The mechanical part 42 is accommodated inside of a casing 55 which is a horseshoe like platy member. On the top surface of the casing 55, the platy substrate (driver 43) is mounted. On the one edge of the platy driver 43, the position sensor 54 (magnetic sensor) is mounted with its magnetic sensing part is protruding outside from the periphery of the casing 55 beyond the opening edge.

The above mechanical part 42 (extendable part 74) comprises a motor 49, a male screw 50 mounted on the shaft of the motor 49, and a nut 51 which moves axially (forward/backward) rotating on the engaged male screw 50. The motor 49 is fixed to the bottom of the casing 55 at its rear part using a clump 57 composed of bolts and nuts. To the bolt of the clamp 57, a socket 53 of a ball joint is fixed.

The nut 51 is covered by a cylindrical magnet 56 which can be fitted to the periphery of the nut. In the vicinity of the center of the cylindrical magnet 56 is annular band like magnetized in S pole. The right and left of the annular band like magnetized S pole is magnetized in annular band like magnetized in N pole. A ball 52 of the ball join is provided on the front edge of the nut 51 and it is accommodated and connected rotatably inside of a socket 53 mounted in the vicinity of the bottom of the casing 55 of the forward segment B. Further, friction resistance between the ball 52 of the ball joint and the casing 55 so as not to rotate the nut 51, when the male screw 50 rotates.

The motion of thus composed moving device 60 is described. The motor 49 acts at the beginning, and then, the male screw 50 rotates, and the nut 51 engaged with the male screw 50 moves rotating along the shaft, thereby the forward segment B is pushed by the ball 52. Since the cylindrical magnet 56 moves axially along the male screw 50 together with the nut 51, the position sensor 54 catches the variation of the poles and detects the end of the action of the extendable part 74.

Figure 9:
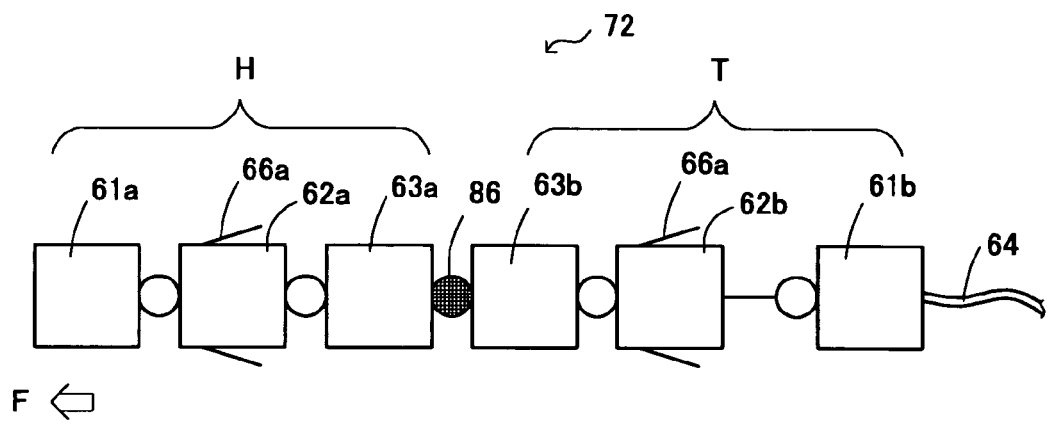
FIG. 9a and FIG. 9b are pattern diagrams showing respectively the conditions of the forward movement and the backward movement of the forth embodiment of the moving device of this invention.
Figure 9:
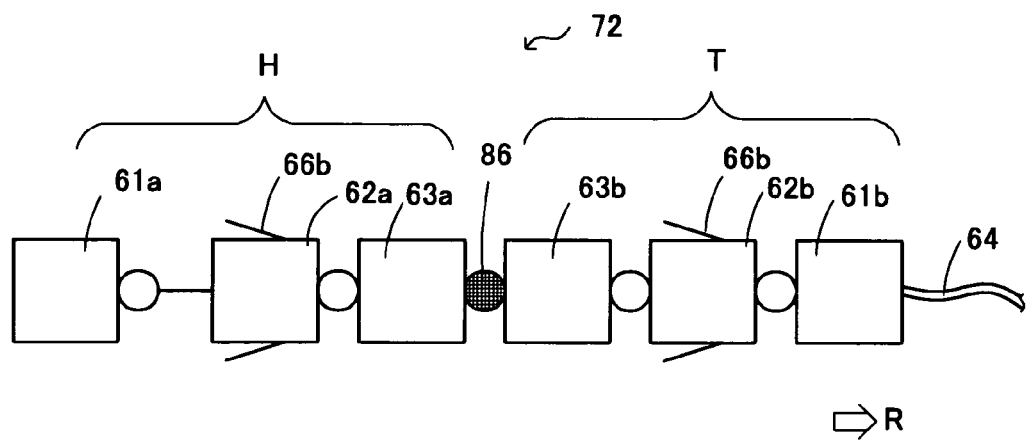

The moving device 72 shown in FIG. 9a comprises a head unit H, and a tale unit T which is interconnected swing-free to a joint 86. The head unit H comprises, starting from the left in FIG. 9a, an edge segment 61a of the head side, an arm segment 62a (front moving part 40b) retractably interconnected to the edge segment 61a, and a drive segment 63a (medium moving part 40c) of the head side retractably interconnected to the arm segment 62a.

The tale unit T comprises a tale side drive segment 63b (medium moving part 40) interconnected swing-free by a joint 86 to a tale side arm segment 63a, a tale side arm segment 62b (end edge moving part 40) retractably interconnected to the drive segment 63b, and a tale side edge segment 61b retractably interconnected to the arm segment 62b. From the edge part of the tale side edge segment 61b, an electric wire 64 to supply a power to the driver of the above drive segment and a signal line to transmit the instruction to move forward/backward from the controller 41 (see FIG. 7) is extended. When the moving device 72 move forward, the later described first arm 66a for moving forward protrudes (see FIG. 9a) from the arm segment 62a, 62b. In the backward movement, the second arm 66b for moving backward protrudes from the same arm segment 62a, 62b (see FIG. 9b).

Figure 10:
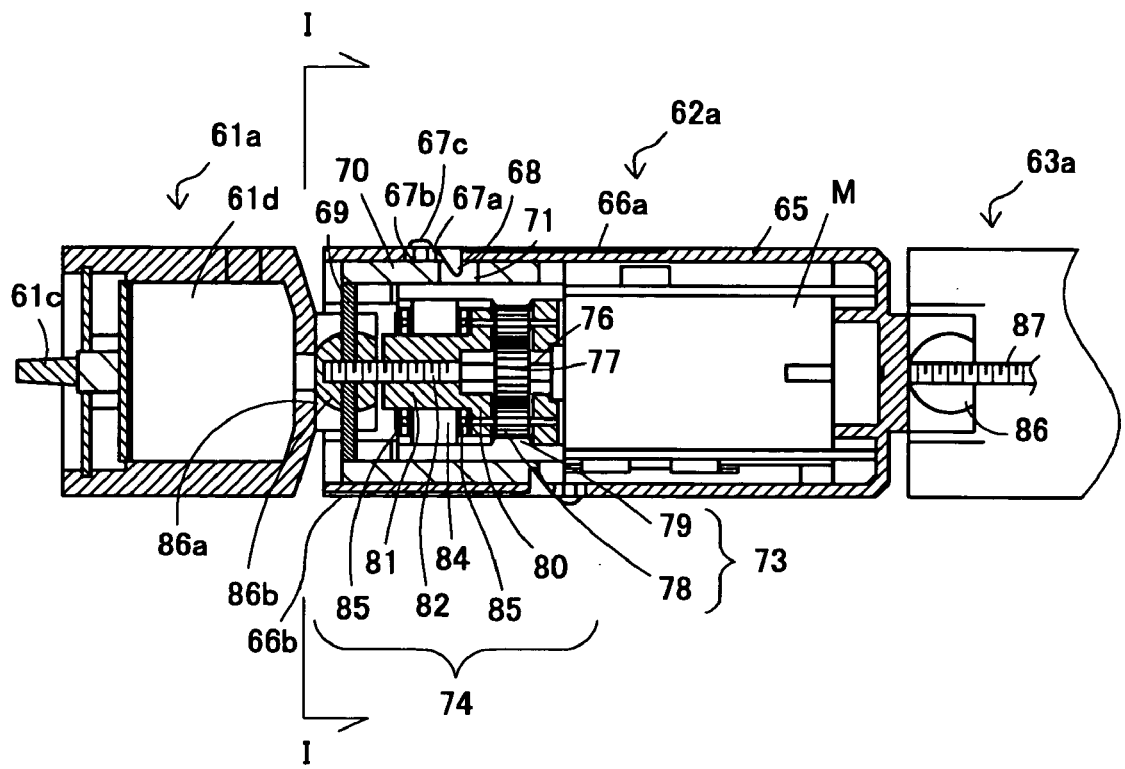
Figure 10:
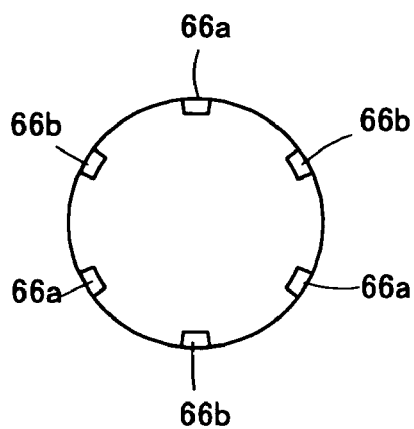

The edge segment 61a shown in FIG. 10a comprises a touch switch 61c provided on its front edge and the controller 61d of the touch switch, and it detects the dead end of pipe lines for automatic stopping etc. Further, in the base edge of the controller 61d, a socket 86a of the ball socket join 86 is provided and interconnected swing-free to a ball 86b mounted to the front edge of the first driving shaft 82 extended from the arm segment 62 later described.

The arm segment 62a comprises a tubular housing 65, an arm 66 mounted on the periphery of the housing 65, a ball join 86 for interconnecting with the driving segment 63 at the right side. The arm 66 comprises the first arm 66a whose front end extends right side having a rotation hinge, for example, in the left side of FIG. 10a, the second arm 66b whose front end extends left side having a rotation hinge in the right side, and a mechanism to open/close the arms.

The each arm has a common structure. As the material, for example, such metal as stainless steel is used and particularly titanium is preferable, which has flexibility and suitable rigidity with low impact on human body. In this embodiment, the arm is made of synthetic resin, and the synthetic resin hinge 67a is connected bendably to the mounting part 67b of the base part of the arm. The mounting part is fixed to the housing 65 with a screw 67c.

In FIG. 10a, the first arm 66a and the second arm 66b are shown one by one. As shown in FIG. 10b, the three first arms 66a are provided around the periphery at an equal interval and the three second arms 66b are provided in between those arms. The number of the arm is not limited to this, and can be one by one, tow by two, or more than four by four. The number of the first arm and the second arm can be different.

In the base part of the arm 66, a cam 68 of which inside is tapered is protruded. And the cam 68 is fitted to a long hole 71 which is formed in a tubular arm holding member 70 provided inside of the housing 65 slidably in the axial direction Inside of the housing 65, a motor M, a reducer 73, and a screw type extendable part 74 which converts the rotation into the extension. To the driving shaft 76 of the motor M, a pinion (sun gear) 77 is fixed, on which perimeter three planet gears 78 engaging with the pinion 77 are located. Outside of the planet gears, an internal gear (ring gear) 79 is located, which is fixed to the housing 65. The planet gears 78 are supported by the carrier 80 rotatably. Accordingly, the reducer 73 composes a planet gear reducer in which the pinion 77 is an input and the carrier 80 is an output.

The extendable part 74 (mechanical part 42) comprises a nut member 81 which is an extended part of the carrier 80, the first driving shaft 82 engaged with the nut member 81. To the left side front edge of the first driving shaft 82, a ball 86b of the ball socket joint 86 is fixed. And to the ball 86b and the edge segment 61a, a pin 69 is connected in the radial direction. The both end of the pin is connected to the above arm holding member 70 rotatably. The extended part of the above internal gear 79 is formed into cylindrical shape, and a thrust cushion 84 lies between the extended part and the nut member 81. A thrust bearing 85, 85 supporting the axial load of the nut member 81 are intervened respectively between the axial one side edge part of the thrust cushion 84 and the carrier 80, and between the other edge part and the thrust cushion 84.

The driving segment 63 is connected to the ball joint 86 by engaging the second driving shaft 87 with the ball joint 86 provided on the right edge of the above arm segment 62. This driving segment 63a is the same as the above described segments excepting that this segment does not have the arm 66 and the mechanism to open/close the arm 66 namely the arm holding member 70 etc. In other wards, as a mechanism to extend/retract the driving shaft, the motor M, the reducer 73, and the extendable part 74 is the same as that of the arm segment. Therefore, the description is omitted.

In the arm segment 62 and the driving segment 63, the driver 43 as shown in FIG. 5b to control the extendable part 74 and the position sensor 54 to detect the each position are provided.

The opposite side edge part of the driving segment 63a in the head unit H is directly connected to the driving segment 63b of the tale unit T by the ball joint 86 without intervention of the driving shaft. Further, the arm segment 62 b and the edge segment 61b is connected in sequence to the back part of the driving segment 63b similarly as described above. (see FIG. 9a, FIG. 9b).

Figure 11:
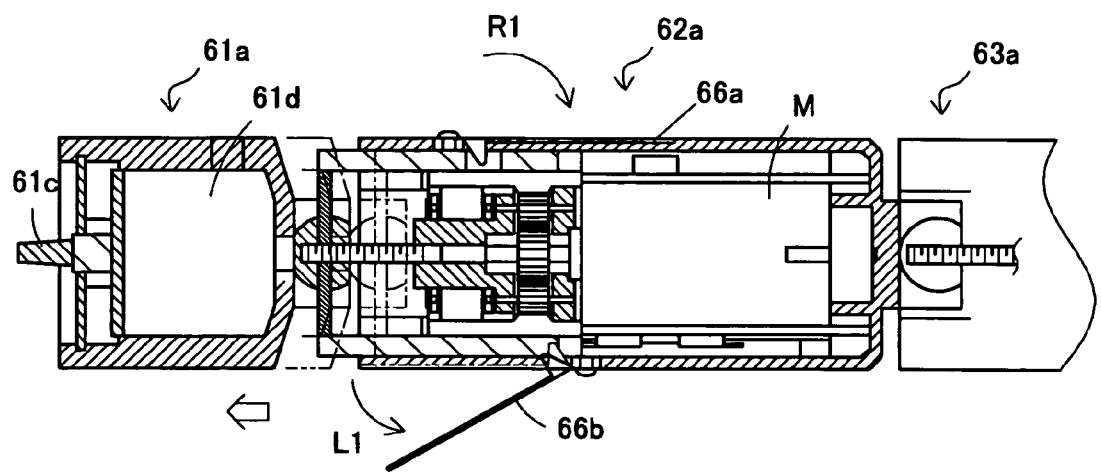
FIG. 11a and FIG. 11b are rough process drawings showing the motion of the each arm segment.
Figure 11:
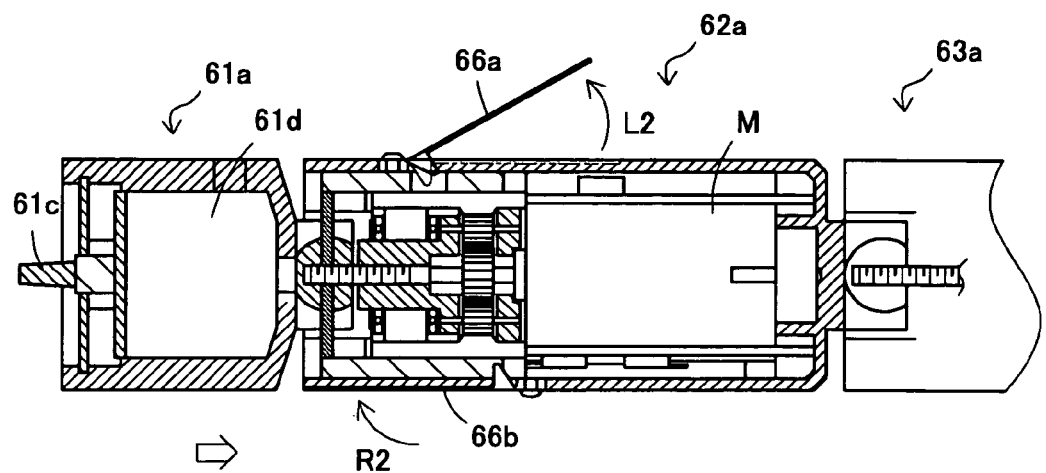

The motion of the arm segment 62 thus composed is described referencing FIG. 10a, FIG. 11, and FIG. 11b. In the condition shown in FIG. 10a, when the motor M rotates, the driving shaft 76 of the motor rotates to rotate the pinion 77, the rotation of the pinion 77 is transferred to the planet gear 78 engaging with the internal gear 79 and rotates the carrier 80 (around the sun gear) which holds the planet gear 78 rotatably (rotatably on its axis). When the carrier 80 rotates, the nut member 81 rotates to push out the first driving shaft 82 (screw side) engaging with the nut member 81 left. The thrust bearing 85 supports the thrusting back force to the carrier 80 which is the reactive force to push out the first driving shaft 82, thereby it makes the rotation of the carrier 80 smooth.

When the first driving shaft 82 is pushed out, the arm holding member 70 engaged with the shaft also acts left. Thereby, the edge part of the long hole 71 pushes the cam of the first arm 66a and the second arm 66b left respectively. In the first arm 66a, being pushed from right, the cam intends to act with the hinge as a shaft in the direction of the arrowhead R1 of FIG. 11a. Inversely, the tapered side of the cam 68 of the arm 66b provided in the under side is pushed left by the right sidewall of the long hole 71 to act with the hinge as a shaft in the direction of the arrowhead L1, thereby the front part being opened. When the first driving shaft 82 is pulled back right, as shown in FIG. 11b, it acts in the reverse procedure as described above, thereby the first arm 66a opens and the second arm 66b closes.

The driving segment 63a does not have the arm 66 and the arm holding member 70 which are provided in the arm segment 62a, but it is substantially same as the arm segment 62a being provided with the motor M, the planet gear reducer 73, the screw type extendable part 74, and the ball socket joint 86, wherein the screw is extended/retracted by the motor rotation. Therefore, detailed description is omitted. The head side driving segment 63a and the tale side driving segment 63b are for extending/retracting the interval between the back and forth arm segment 62a, 62b and for interconnecting swing-free the head unit H and the tale unit T to make the movement in curved pipe lines smooth.

Figure 12:
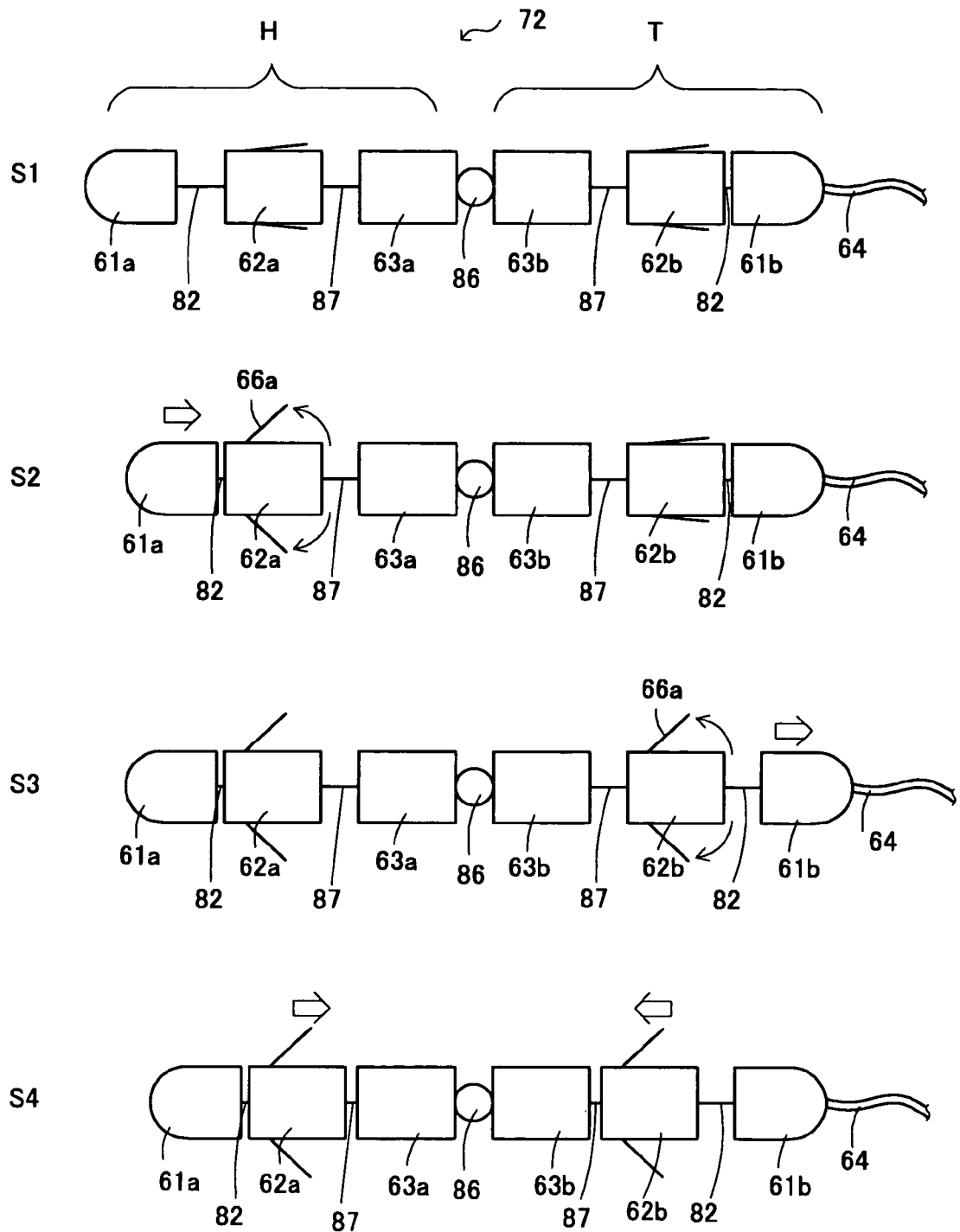
FIG. 12 is a rough process drawing showing the reset motion of the moving device of FIG. 9.

The motion of the moving device 72 thus composed is described. In FIG. 12 a reset action to prepare for the movement of the moving device 72 is shown. In the first process S1 in FIG. 12, a condition is shown, in which the first driving shaft 82 and the second driving shaft 87 in the head side are at their limits of extension, and at the same time, the second driving shaft 82 in the tale side is in the condition of being pulled back and the second driving shaft 87 is at its limit of extension. Starting from this condition, as shown in the second process S2, the arm segment 62a in the head side pulls in the edge part segment 61a in the head side. At this time the first arm 66a opens. And then, as shown in the third process S3, the first driving shaft 82 is pushed out from the arm segment 62b in the tale side, the edge part segment 61b in the head side is pushed out to open the first arm 66a.

Operating as just described, the first arm 66a responsible for the forward movement opens. And then, the driving segment 63a, 63b in the head side and the tale side drive the second driving shaft 87 so as to fetch in it, and as shown in the forth process S4, pulls in the arm segment 62a, 62b respectively. These sequent motions are the reset action to move toward the head side.

When it is moved toward the tale side (move backward), the above described reset action is reversed in head H and tale T to open the second arm 66b, which is the reset action to move backward.

Figure 13:
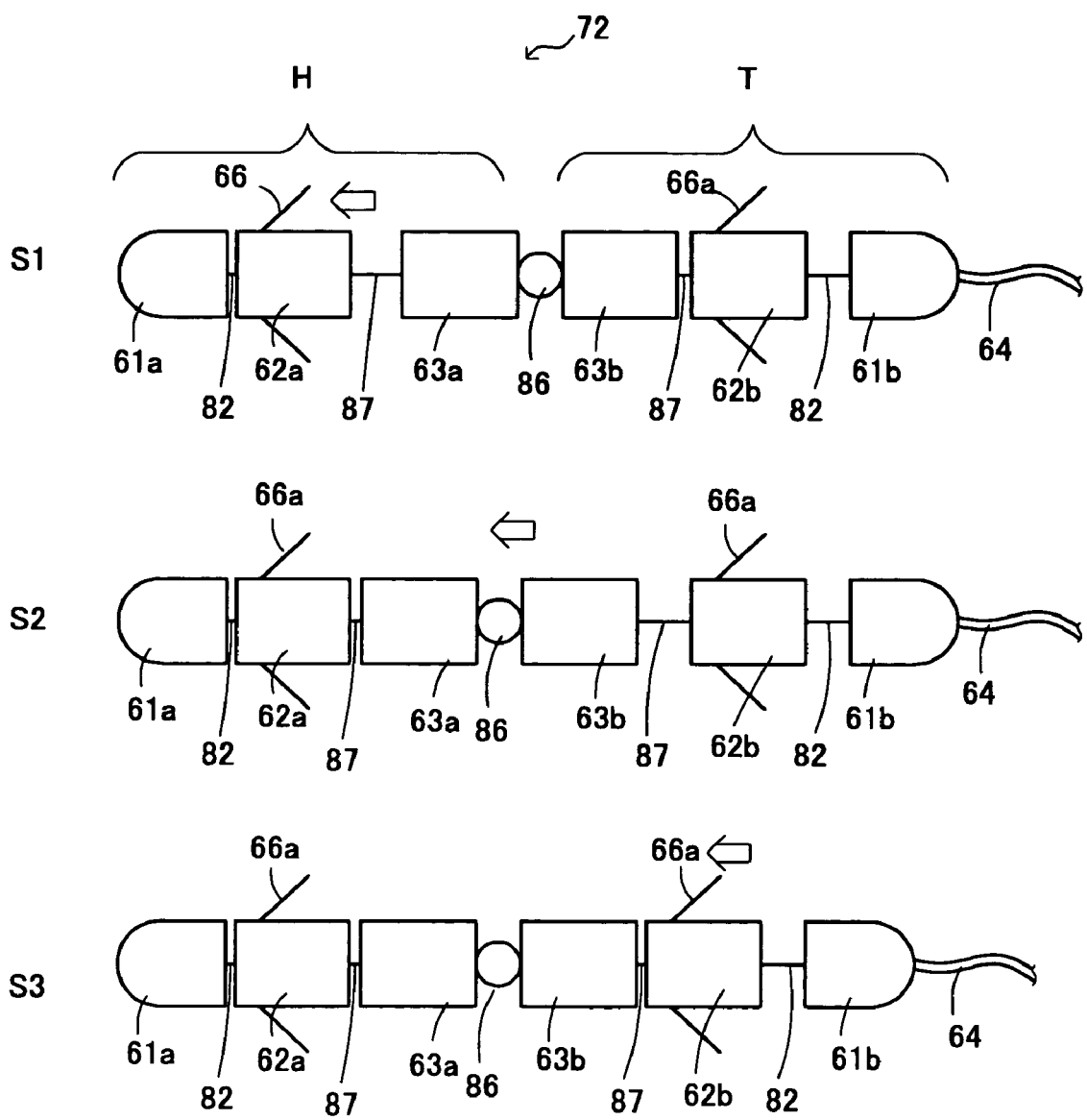
FIG. 13 is a rough process drawing showing the forward movement of the moving device; and FIG. 14a and FIG. 14b is another embodiment of the moving device of FIG. 13

The motion of the moving device 72 thus reset is described referencing FIG. 13. The rough process drawing shown in FIG. 13 is the case of the forward movement. Starting from the condition as shown in FIG. 12 that the reset is completed, as shown in the first process of FIG. 13, the head driving segment 63a pushes out the head segment 62a. At the same time, the arm 66a extending from the tale arm segment 62b holds on to the inside of pipe lines, thereby the head side arm segment 62a is pushed out by the reactive force.

Next, the head side driving segment 63a pull in the head side arm segment 62a, at the same time, the tale side driving segment 63b pushes out the tale side arm segment 62b. At this time also, the arm 66a extending from the arm segment 62b holds on, thereby the two driving segment 63a, 63b move toward the head side by the reactive force. And then, as shown in the third process S3, the tale side driving segment 63b pulls back the tale side arm segment 62b to return to the first process S1. At this time, inversely the arm 66a of the head side arm segment 62a holds on at its front edge, which supports the reactive force of the pulling action of the tale side arm segment 63b.

By repeating these processes, the moving device 72 moves forward wholly. When it moves backward, after the above described reset action is completed, the above described process is performed with its head unit H and tale unit T reversed. The operation of the motor rotation i.e. normal/reverse/stop in the each segment of the above described operation can be done from the outside of pipe lines via the electric wire 64 shown in FIG. 9. In the case that a wireless communication is used, the electric wire is not necessary.

In the embodiment described above, the edge segment 61a is provided in front of the head side segment 63a, and the edge segment 61b is provided in the back of the tale side segment 63b, but the forward and backward movement can be done without the edge segment 61a, 61b.

Further, the forward and backward movement can be done without either the head side segment 63a or the tale side segment 63b. But, interconnecting the two driving segment 63a, 63b mutually by the ball joint 86 allows smooth movement in a curved part.

Moreover, omitting the driving segment 63a, 63b, arms for forward and backward movement can be provided in one segment. In this case, since the length of the segment is long, it is preferable to separate them and to interconnect them mutually using a joint for smooth movement in a curved part.

In the embodiment described above, as a means to hold on to the inside of pipe line, the arm 66a, 66b extending from the arm segment 62a, 62b are employed.

Figure 14:
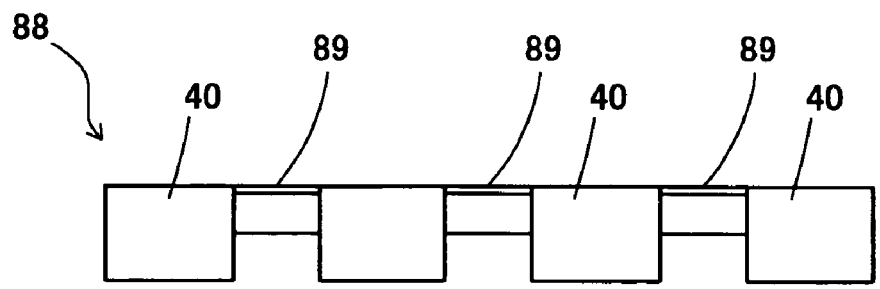
FIG. 14c is a partial perspective view of the FIG. 14b.
Figure 14:
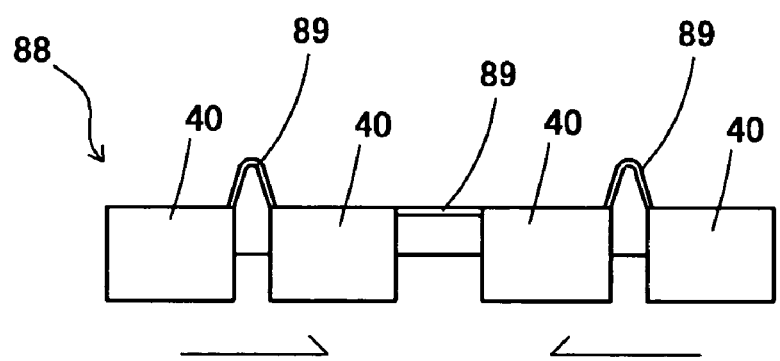
Figure 14:
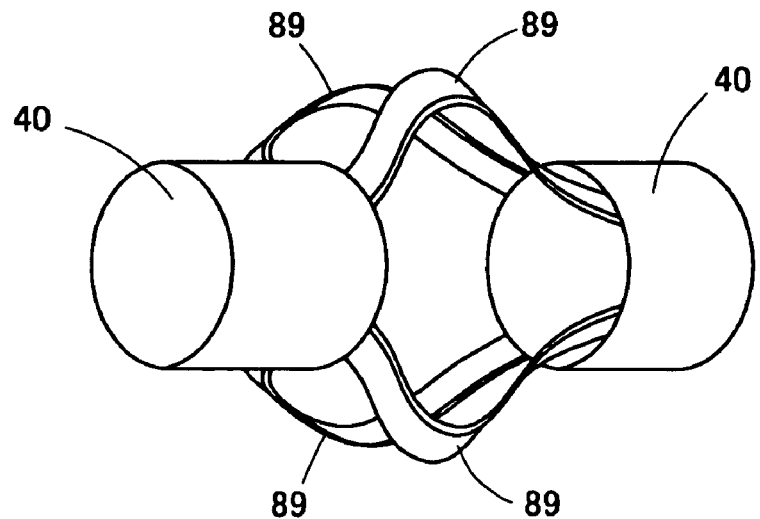

But in the moving device 88 of FIG. 14a, the neighboring segments (the moving device) 40 are connected to each other by the flat strip plate 89, which reacts as the means to hold on to the inside of the pipe line. The moving device 88 converts into the retracting condition (FIG. 14b) from the extending condition (FIG. 14a) by bending or curving the flat strip palate 89. This action of the flat strip plate 89 widens the outer diameter of the moving device 88. Therefore, the top of the curved strip plate 89 can press the inside of the pipe line and enables the moving device to abut and to hold the inside of the pipe line.

In the embodiment using the flat strip plate 89, the neighboring segments 40 may be connected to each other by four flat strip plates 89 employed around the periphery of the segment 40 at equal interval, like shown in FIG. 14c.

As for a material of the flat strip plate 88, for example, material such as stainless steel and preferably titanium or titanium alloys, which has flexibility and has suitable rigidity with low impact on human body, may be used.

What is claimed is:

1. A moving device in pipe lines, comprising:
    an inside magnet line in which three or more magnet elements are interconnected in the direction of magnet flux;
    an outside magnet element line which is provided slidably on the outside of the magnet elements of the inside magnet line;
    a switching means which switches the magnet poles of the inside magnet elements and the corresponding pair of the outside magnet elements in-phase or reversed phase; and
    a control means for controlling the each switching means by a preset program;
    wherein said preset program instructs said switching means to switch the magnet poles of the inside magnet elements and/or the corresponding pair of the outside magnet elements to move the outside magnet elements via the attractive force and repelling force of the magnet poles; and
    wherein the movement of the outside magnet elements is a driving force for the movement of the moving device.

2. A moving device in pipe lines according to claim 1, wherein the inside magnet elements are interconnected flexibly each other.

3. A moving device in pipe lines according to claim 1, wherein the switching means comprises an electromagnet provided at least on one side of the corresponding pair of the magnet elements and a distributor for selecting the magnetic pole of the electromagnet.

4. A moving device in pipe lines, comprising:
    a magnet line in which three or more electromagnets are interconnected;
    a guide member which guides the magnet lines slidably; and
    a distributor for controlling the magnet poles of said electromagnets by a preset program;
    wherein said preset program instructs said distributor to switch the magnet poles of said electromagnets to move the electromagnets via the attractive force and repelling force of the magnet poles; and
    wherein the movement of the electromagnets is a driving force for the movement of the moving device.

5. A moving device in pipe lines according to claim 4, wherein the guide member is a linear body let through the center of the magnets slidably and any of the electromagnets is fixed to the linear body.

6. A moving device in pipe lines according to claim 5, wherein the linear body is flexible.

7. A moving device in pipe lines according to claim 1, 2 or 3, wherein the control means comprises a controlling part which is located in the each switching means and a controller which gives instructions to move to the controlling part of the end magnet element pairs; the controlling part of the above pair of the magnet elements comprises a receiving part for receiving instructions to move, an operation part which performs an arithmetic operation of the magnets by the program in which the instructions to move obtained from the receiving part and the information of the object magnet pole of the magnet element are used as an argument, and a transmitting part which transmits the instructions to move to the next pair of the magnet elements after the switching part switches the magnet poles according to the operation part; the receiving part and the transmitting part transmits the instructions to move from the end pair of the magnet element to the front pair or from the front pair of the magnet element to the end pair in sequence.

8. A moving device in pipe lines, comprising:
    a magnet line in which three or more electromagnets are interconnected;
    a guide member which guides the magnet lines slidably; and
    a distributor for controlling the magnet poles of said electromagnets by a preset program,
    wherein the distributor is located in each electromagnet and comprises the controlling part to control the poles of the electromagnet by a preset program and the controller which gives instructions to the controlling part of the end distributor; the controlling part of the electromagnet is provided with the receiver which receives the instructions to move, the operation part which performs an arithmetic operation of the magnets and controls the magnets by the program in which the instructions to move obtained from the receiving part and the information of the object magnet pole of the magnet element are used as an argument, and is provided with the transmitter which transmits the instructions to move to the controlling part of the electromagnet after the control of the pole by the operation parts; the receiving part and the transmitting part transmit the instructions to move from the end electromagnets to front electromagnets or from the front electromagnets to the end electromagnets.

9. A moving device in pipe lines, comprising:
    three or more segments;
    an interconnecting means which interconnects these segments;
    a driving means which drives the interconnecting means so as to move these segments to the remaining segments relatively; and
    a control means to control the driving means,
    wherein the controlling means comprises a controlling parts provided in each segment and a controller which gives instructions to move to the end controlling part; the controlling part comprises a receiving part which receives instructions to move, an operation part which drives the driving means by computing the conditions of the object driving means using the information of the instructions to move obtained from the receiving part and the conditions of the object driving means as an argument, and a transmitting part which transmits the instructions to move to the controlling part of the other driving means after the control of the driving means by the operation part; the each receiving part and the transmitting part transmits the instructions to move from the end driving means to the front driving means or from the front driving means to the end driving means in sequence; the engaging force with the inside of pipe lines of the moved segments are smaller than that of the remaining segments.

10. A moving device in pipe lines, comprising:
    three or more segments;
    an extendable interconnecting means which interconnects these segments in a straight line retractably; and
    an extendable driving means for driving the extendable interconnecting means so as to move these segments selectively to the remaining segments relatively, wherein the engaging force with the inside of pipe lines of the moved segments are smaller than that of the remaining segments, wherein the extendable driving means drive the extendable interconnecting means by switching magnet poles of said segments to move these segments via the attractive force and repelling force of the magnet poles; and wherein the movement of these segments is a driving force for the movement of the moving device.

11. A moving device in pipe lines according to claim 10, wherein each force of engaging with the inside of pipe lines of the segments is equal.

12. A moving device in pipe lines according to claim 10 or 11, wherein the extendable driving means in means for moving the each segment forward or backward selectively to the remaining segments.

13. A moving device in pipe lines according to claim 10, wherein the extendable driving means moves the segments from one edge to another edge in sequence.

14. A moving device in pipe lines according to claim 10, wherein an arm for moving forward whose engaging force inside the pipe lines for moving forward is larger than that for moving backward is provided.

15. A moving device in pipe lines according to claim 14, wherein an arm for moving backward whose engaging force inside the pipe lines for moving backward is larger than that for moving forward is provided for at least one of the segments, and a direction selecting mean for selectively moving the arms for moving forward and backward is provided.

16. A moving device in pipe lines, comprising;
an edge segment of the head side;
an edge segment of the tale side;
an extendable interconnecting means which interconnects these segments mately retractably and
an extendable driving means which drives the extendable interconnecting means,
wherein the arm for forward moving is provided, the engaging force with the inside of pipe lines of which being larger than backward, wherein the extendable driving means drive the extendable interconnecting means by switching magnet poles of said segments to move these segments via the attractive force and repelling force of the magnet poles; and wherein the movement of these segments is a driving force for the movement of the moving device.

17. A moving device in pipe lines according to claim 16, wherein the arm for moving backward is provided on each segment, the engaging force with the inside of pipe lines of which being larger than backward.

18. A moving device in pipe lines according to claim 16, wherein an edge segment is swing-freely and retractably interconnected to the back of the tale side segment, an extendable driving means provided between the edge segment and the tale side segment.

19. A moving device in pipe lines according to claim 17, wherein an edge segment is swing-freely and retractably interconnected to the front of the head side segment, an extendable driving means provided between the edge segment and the head side segment.

20. A moving device in pipe lines according to claim 16, wherein a storage in which movement patterns of the segment and a controlling part which controls the movement of segments according to movement patterns of segments are provided.

21. A moving device in pipe lines according to claim 8, wherein the guide member is a linear body let through the center of the magnets slidably and any of the electromagnets is fixed to the linear body.

22. A moving device in pipe lines according to claim 8, wherein the linear body is flexible.

* * * * *